(12) United States Patent
Shahidi et al.

(10) Patent No.: US 9,018,248 B2
(45) Date of Patent: Apr. 28, 2015

(54) FATTY ACID DERIVATIVES OF CATECHINS AND METHODS OF THEIR USE

(75) Inventors: Fereidoon Shahidi, St. John's (CA); Ying Zhong, Fort Collins (CA)

(73) Assignee: Genesis Group Inc., St. John's Newfoundland & Labrador (CA)

( * ) Notice: Subject to any disclaimer, the term of this patent is extended or adjusted under 35 U.S.C. 154(b) by 0 days.

(21) Appl. No.: 13/639,795

(22) PCT Filed: Apr. 8, 2011

(86) PCT No.: PCT/CA2011/000376
§ 371 (c)(1),
(2), (4) Date: Oct. 5, 2012

(87) PCT Pub. No.: WO2011/123942
PCT Pub. Date: Oct. 13, 2011

(65) Prior Publication Data
US 2013/0030047 A1 Jan. 31, 2013

Related U.S. Application Data

(60) Provisional application No. 61/322,004, filed on Apr. 8, 2010.

(51) Int. Cl.
| | | |
|---|---|---|
| A61K 31/35 | (2006.01) |
| A61P 35/00 | (2006.01) |
| A61P 29/00 | (2006.01) |
| A61P 9/10 | (2006.01) |
| A61P 31/12 | (2006.01) |
| C07D 311/62 | (2006.01) |

(52) U.S. Cl.
CPC .................................. *C07D 311/62* (2013.01)

(58) Field of Classification Search
CPC .................................................... C07D 311/62
USPC ........................................ 544/399; 514/456
See application file for complete search history.

(56) References Cited

U.S. PATENT DOCUMENTS

| 7,544,816 B2 | 6/2009 | Chan et al. |
| 2003/0105030 A1 | 6/2003 | Liao et al. |
| 2008/0058409 A1 | 3/2008 | Fukami et al. |
| 2011/0003889 A1* | 1/2011 | Kaihatsu et al. ............... 514/456 |

OTHER PUBLICATIONS

Wermuth, C.G., Glossary of Terms Used in Medicinal Chemistry (1998) Pure & Appl. Chem. 70(5): 1129-1143.*
Cong-Cong, L., Chemical Modification on Tea Polyphenols and Study on Lipid-Soluble Tea Polyphenols, Master's Thesis, Shanghai Jiaotong University, 2008. p. 1-73.*
Zhang, X., Preparation and Chemical Modification on Tea Polyphenols and the Study on the Antioxidant Activity of the Liposoluble Tea Polyphenols, Master's Thesis, Department of Chemical Engineering, Northwestern University (Xian City, China), 2004, p. 1-62.*
Cong-Cong, L., Chemical Modification on Tea Polyphenols and Study on Lipid-Soluble Tea Polyphenols, Master's Thesis, Shanghai Jiaotong University, 2008., Partial English Translation, p. 1-3.*
Zhang, X., Preparation and Chemical Modification on Tea Polyphenols and the Study on the Antioxidant Activity of the Liposoluble Tea Polyphenols, Master's Thesis, Department of Chemical Engineering, Northwestern University (Xian City, China), 2004, Partial English Translation, p. 1-2.*
Jacobson, K.A., Adenosine analogs with covalently attached lipids have enhanced potency at A1-adenosine receptors, 1987, FEBS Lett. 225, (1,2), 97-102.*
Matsubara, K. et al. Catechin Conjugated with Fatty Acid Inhibits DNA Polymerase and Angiogenesis. DNA and Cell Biology. 25(2):95-103, 2006.
Zhong, Y. and Shahidi, F. Fish in a tea pot: Do catechin-omega 3 PUFA esters offer additional benefits? ISNFF Annual Meeting 2009, San Franciso, CA, Nov. 1-4, 2009.
Zhong, Y. and Shahidi, F. Antioxidant and anti-inflammatory activities of green tea catechin derivatives. 2nd Newfoundland Nutrigenomics Conference, St.John's, NL, Jun. 2009.
Zhong, Y., Pan, M.H. and Shahidi, F. Antioxidant and anti-inflammatory activities of EGCG (epigallocatechin gallate) derivatives. IFT Annual Meeting 2009, IFT Annual Meeting + FOOD ExXPO®, Anaheim, CA, Jun. 6-9, 2009.
Zhong, Y. and Shahidi, F. Antioxidant activity of epigallocatechin gallate (EGCG) fatty acid esters. IFT Annual Meeting 2008, IFT Annual Meeting + FOOD EXPO®, New Orleans, LA, Jun. 28-Jul. 2, 2008.
Zhong, Y. and Shahidi, F. Antioxidant activity of esters of epigallocatechin gallate (EGCG). 14th World Congress of Food Science & Technology, Shanghai, China, Oct. 19-23, 2008.
Kaihatsu, K. et al. Broad and Potent Anti-Influenza Virus Spectrum of Epigallocatechin-3-O-Gallate-Monopalmitate. Journal of Molecular and Genetic Medicine. 3(2): 195-197, 2009.
Wanasundara, U.N. and Shahidi, F. Stabilization of Seal Blubber and Menhaden Oils with Green Tea Catechins. Journal of American Oil Chemists Society. 73(9):1183-1190, 1996. (Abstract).
Decker, E.A. et al., J. Agric. Food Chem., 38:674-677, 1990.
Huang et al. J. Agric. Food Chem. 50:1815-1821, 2002.
Shahidi, F. and Hong. C. Evaluation of Malonaldehyde as a Marker of Oxidative Rancidity in Mean Products. J. Food Biochem. 15:97-105, 1991.
Zhong, Y. and Shahidi, F. Modified Tea Catechins in Oxidation Control. AOCS Annual Meeting & Expo May 16-19, 2010. Memorial University of NewFoundland, St. John's , NL, Canada. Abstract published Dec. 17, 2009.

(Continued)

*Primary Examiner* — Noble Jarrell
*Assistant Examiner* — John Mauro
(74) *Attorney, Agent, or Firm* — Riverside Law LLP

(57) ABSTRACT

The present disclosure relates to fatty acid derivatives of green tea catechins including epicatechin (EC), epicatechin gallate (ECG), epigallocatechin (EGC), epigallocatechin gallate (EGCG) and their epimers (e.g., catechin, catechin gallate, gallocatechin, gallocatechin gallate) or their mixtures and/or green tea extracts.

18 Claims, 12 Drawing Sheets

(56) References Cited

OTHER PUBLICATIONS

Lambert, et al., "Peracetylation as a Means of Enhancing in Vitro Bioactivity and Bioavailability of Epigallocatechin-3-Gallate," *Drug Metabolism and Disposition*, 2006, 34:2111-2116.

Hon Lung Kok, et al., "In vitro cytotoxicity of (−)-EGCG octaacetate on MDAMB-231 and SKHep-1 human carcinoma cells: A pharmacological consideration on prodrug design," *International Journal of Molecular Medicine*, 2008, 22:841-845.

Mori, et al., "Enhanced anti-influenza A virus activity of (−)-epigallocatechin-3-O-gallate fatty acid monoester derivatives: Effect of alkyl chain length," *Bioorganic & Medicinal Chemistry Letters*, 2008, 18:4249-4252.

Matsumura, et al., "Enhanced antitumor activities of (−)-epigallocatechin-3-O-gallate fatty acid monoester derivatives in vitro and in vivo," Biochemical and Biophysical Research Communications, 2008, 377:1118-1122.

* cited by examiner

Hydroxyl radical induced DNA scission (lane 1: DNA only; lane 2: DNA + FeSO₄ + H₂O₂; lane 3: DNA + FeSO₄ + H₂O₂ + EGCG; lane 4: DNA + FeSO₄ + H₂O₂ + compound 1a; lane 5: DNA + FeSO₄ + H₂O₂ + compound 1b; lane 6: DNA + FeSO₄ + H₂O₂ + compound 1c.

Peroxyl radical induced DNA scission (lane 1: DNA only; lane 2: DNA + AAPH; lane 3: DNA + AAPH + EGCG; lane 4: DNA + AAPH + compound 1a; lane 5: DNA + AAPH + compound 1b; lane 6: DNA + AAPH + compound 1c

(C: negative control; +: positive control, AOM only)

(*, P<0.05; , P<0.01; *, P<0.001 compared with the LPS treatment only; #, P<0.001 compared with the control)

(*, $P<0.05$; , $P<0.01$; *, $P<0.001$ compared with the LPS treatment only; #, $P<0.001$ compared with the control)

(C: negative control without LPS; + : positive control with LPS)

(C: negative control without LPS; + : positive control with LPS).

FATTY ACID DERIVATIVES OF CATECHINS AND METHODS OF THEIR USE

CROSS-REFERENCE TO RELATED APPLICATION

The present application is a national stage application of and claims priority to International Application No. PCT/CA2011/000376, filed Apr. 8, 2011, and published under PCT Article 21(2) in English, which claims priority from U.S. Provisional Application No. 61/322,004, filed on Apr. 8, 2010, all of which are incorporated by reference in their entireties herein.

FIELD OF THE DISCLOSURE

The present disclosure relates to fatty acid derivatives of catechins.

BACKGROUND OF THE DISCLOSURE

Tea, a product made from the leaves and buds of a plant, such as *Camellia sinensis*, is a popular beverage worldwide and a major source of dietary flavonoids. Tea also confers health benefits to humans such as lowering cholesterol and enhancing insulin activity. In addition, tea is considered an antioxidant, antimicrobial, as well as antiviral material and also possesses immunomodulatory and anti-carcinogenic properties. Accordingly, tea is considered a functional food beverage and therapeutic aid in many diseases. Polyphenols, particularly flavonoids, which comprise approximately 30% of the dry weight of the leaves, are among the major active components responsible for the beneficial properties of tea. Epigallocatechin gallate (EGCG) is the predominant flavonoid (flavan-3-ol or catechin) present in green tea polyphenols at a level of about 60%, while epicatechin (EC), epicatechin gallate (ECG) and epigallocatechin (EGC) are also present.

SUMMARY OF THE DISCLOSURE

It has now been determined that the esterification of EGCG with fatty acids provides a way to increase the lipophilicity of EGCG, which allows for the application of the modified compounds in oil and emulsion systems in which EGCG and other catechins are insoluble or sparingly soluble. Accordingly, the increase in lipophilicity of EGCG increases the cellular absorption and bio-efficiency of EGCG, and accordingly, leads to increased beneficial effects when fatty acid derivatives of EGCG are administered.

Accordingly, the present disclosure relates to a compound of the formula (I):

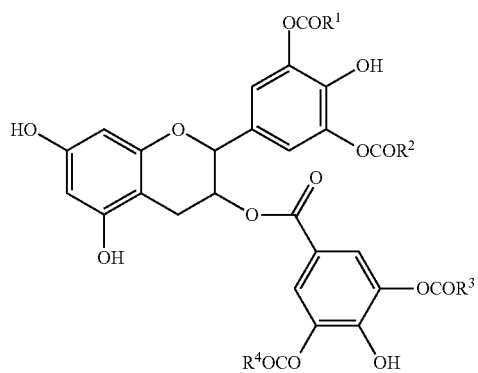

(I)

wherein $R^1$, $R^2$, $R^3$ and $R^4$ are independently or simultaneously $C_{1-3}$alkyl, $C_{2-3}$alkenyl or an unsaturated or saturated aliphatic moiety of medium or long chain fatty acid, or a pharmaceutically acceptable salt, prodrug, solvate or regio- or stereoisomer thereof.

In another embodiment, the unsaturated or saturated aliphatic moiety of long chain fatty acid contains between 13 and 21 carbon atoms. In another embodiment, the unsaturated or saturated aliphatic moiety of long chain fatty acid contains zero, one, two, three, four, five or six double bonds. In a further embodiment, the unsaturated or saturated aliphatic moiety of long chain fatty acid is selected from the formula (i), (ii), (iii) and (iv)

$$—(CH_2)_{16}CH_3 \quad (i)$$

$$—(CH_2)_3(CH=CHCH_2)_5CH_3 \quad (ii)$$

$$—(CH_2)_2(CH=CHCH_2)_6CH_3 \quad (iii)$$

$$—(CH_2)_5(CH=CHCH_2)_5CH_3 \quad (iv).$$

In another embodiment, $R^1$, $R^2$, $R^3$ and $R^4$ are propyl.

In another embodiment, $R^1$, $R^2$, $R^3$ and $R^4$ independently or simultaneously comprise a saturated or an unsaturated aliphatic moiety of long chain fatty acid.

In another embodiment, $R^1$, $R^2$, $R^3$ and $R^4$ are simultaneously $C_{1-3}$alkyl, $C_{2-3}$alkenyl or an unsaturated or saturated aliphatic moiety of a medium- or long-chain fatty acid.

In another embodiment, $R^1$, $R^2$, $R^3$ and $R^4$ are simultaneously or independently an unsaturated or saturated aliphatic moiety of a medium-chain fatty acid. In a further embodiment, the aliphatic moiety of the medium chain fatty acid is derived from an caprylic acid, caproic acid or lauric acid.

In another embodiment of the disclosure, the compound of the formula (I) comprises

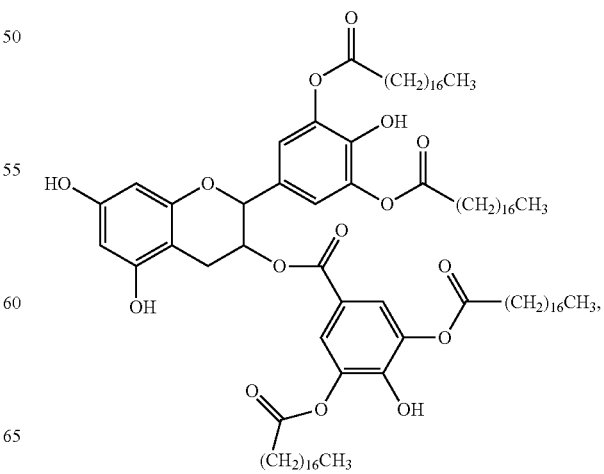

-continued

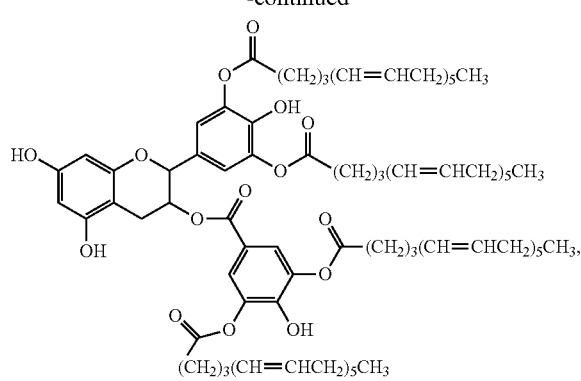

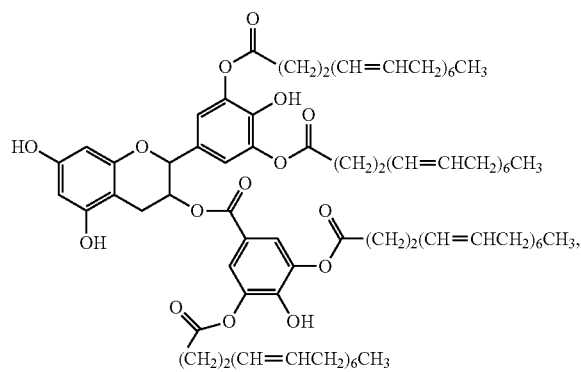

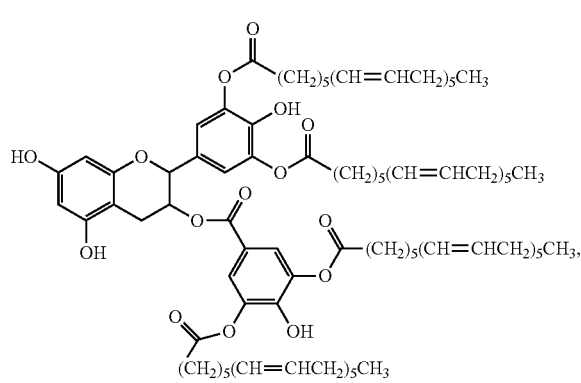

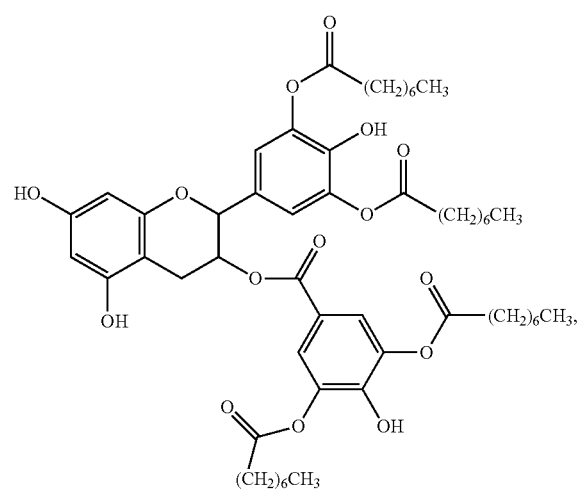

-continued

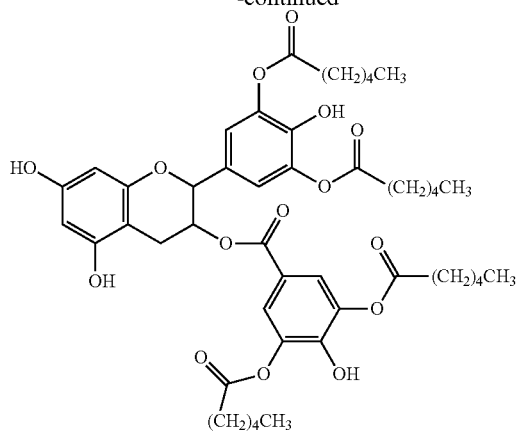

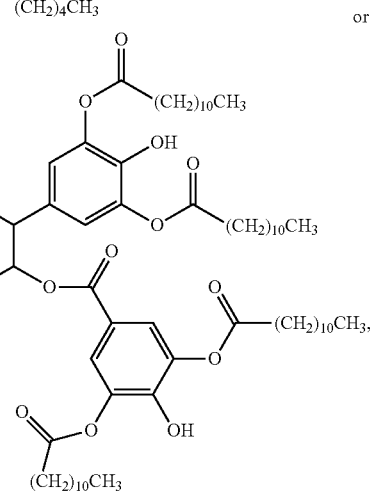

and their isomers thereof.

In an embodiment of the disclosure, there is also included a method for the treatment of atherosclerosis with a therapeutically effective amount of a compound of the disclosure in mammals. In another embodiment, the compounds of the disclosure possess an inhibitory effect against LDL-cholesterol oxidation.

In an embodiment of the disclosure, there is further a method for the treatment of inflammation with a therapeutically effective amount of a compound of the disclosure in mammals. In another embodiment, the compounds of the disclosure possess an inhibitory effect against lipopolysaccharides (LPS)-induced inflammation.

In an embodiment of the disclosure, there is also a method for the treatment of a viral infection with a therapeutically effective amount of a compound of disclosure in mammals. In another embodiment, the viral infection comprises a hepatitis infection, optionally a hepatitis C infection, and a HIV infection. In another embodiment, the compounds of the disclosure possess an inhibitory effect against virus maturation and infection.

In another embodiment of the disclosure, there is provided a method for the prevention or treatment of cancer in a mammal comprising administering to the mammal a therapeutically effective amount of a compound of the disclosure. In another embodiment, the cancer comprises colon cancer.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

The present disclosure will now be described in greater detail with reference to the following drawings in which.

DESCRIPTION (I) Definitions

Figure 1:
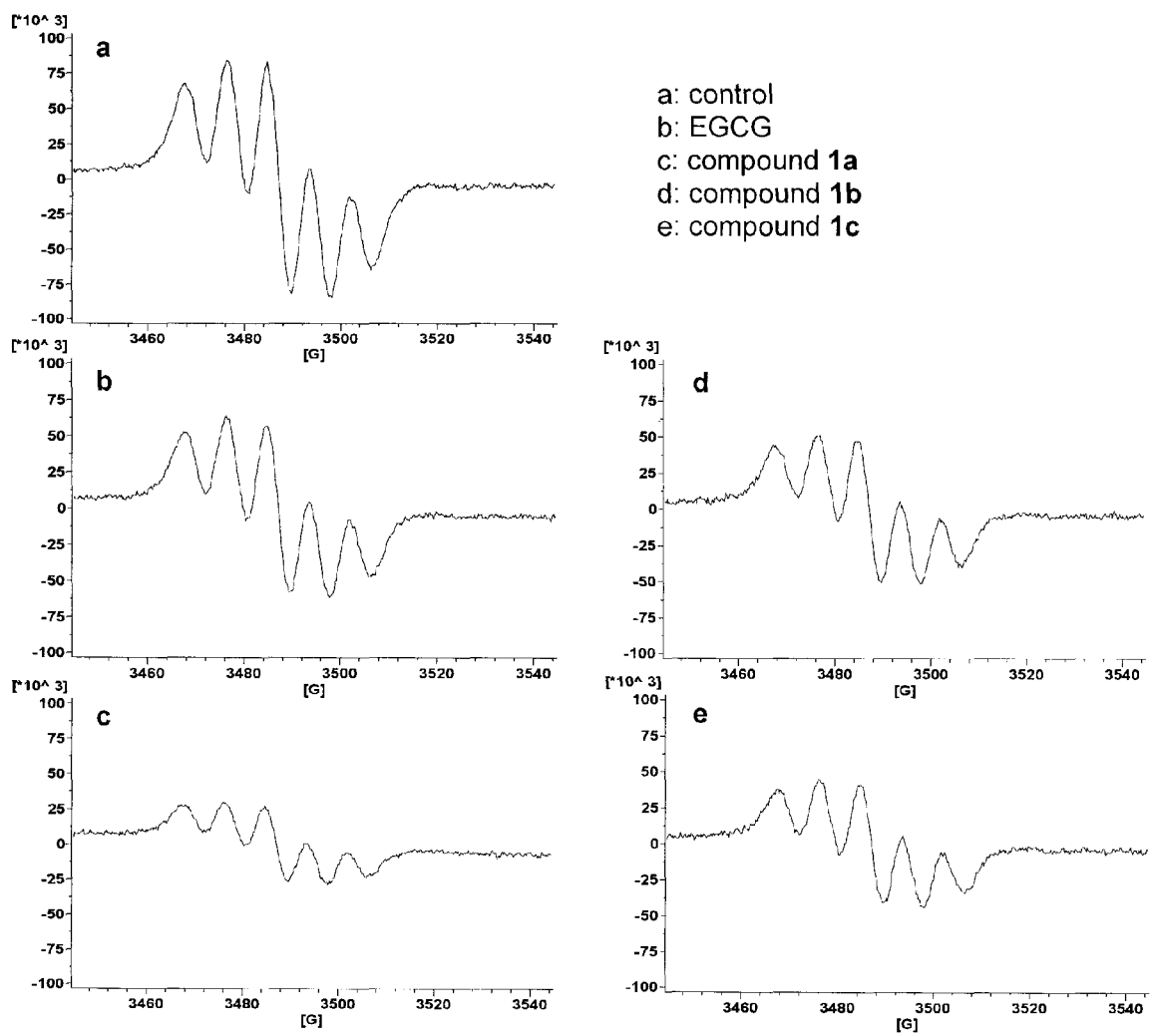
FIG. 1 shows the EPR spectra of DPPH radical as affected by compounds of the formula (I)
Figure 2:
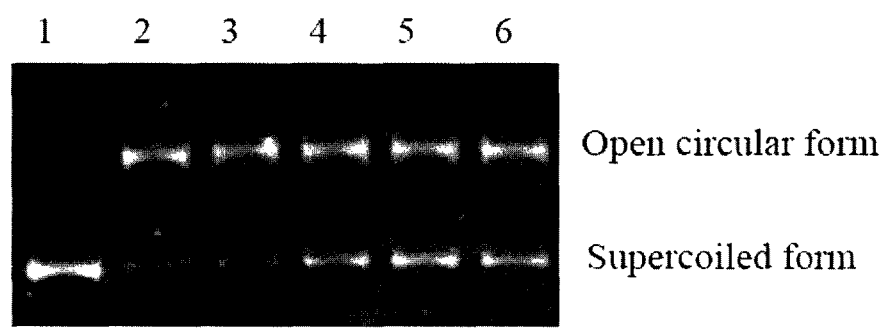
FIG. 2 shows the antioxidant activity of compounds of the formula (I) in hydroxyl radical-induced DNA scission.

The term "$C_{1-3}$alkyl" as used herein means straight and/or branched chain, saturated alkyl groups containing from one to three carbon atoms and includes methyl, ethyl, propyl and isopropyl.

The term "$C_{2-3}$alkenyl" as used herein means straight and/or branched chain, unsaturated alkenyl groups containing from one to three carbon atoms and one double bond, and includes vinyl, 1-propenyl and 2-propenyl.

The terms "unsaturated or saturated aliphatic moiety of short chain fatty acid", "unsaturated or saturated aliphatic moiety of medium chain fatty acid" and "unsaturated or saturated aliphatic moiety of long chain fatty acid" as used herein refers to aliphatic (saturated or unsaturated) tail which is bonded to the carboxylic acid moiety of a fatty acid. It is known to those skilled in the art that a fatty acid comprises a carboxylic acid moiety (C(=O)OH) which is bonded to a saturated or unsaturated aliphatic carbon chain, which contains between, for example, 2 carbon atoms to 5 carbon atoms for a short chain fatty acid, 5 carbon atoms to 13 carbon atoms for a medium chain fatty acid and 13 carbon atoms to 21 carbon atoms for a long chain fatty acid. For example, caprylic acid is a fatty acid containing a carboxyl moiety bonded to a saturated 7-carbon aliphatic chain. As such, the fatty acid caprylic acid ($CH_3(CH_2)_6COOH$) comprises a carboxylic acid moiety and a seven-carbon hydrocarbon chain. Stearic acid ($CH_3(CH_2)_{16}COOH$) contains a seventeen-carbon hydrocarbon chain bonded to a carboxylic acid moiety, while all-cis-5,8,11,14,17-eicosapentaenoic acid (an omega-3 fatty acid) comprises a carboxylic acid moiety bonded to an unsaturated 19-carbon hydrocarbon chain, which possesses five cis double bonds. An unsaturated hydrocarbon chain refers to a chain possessing one or more, optionally one to six, double and/or triple bonds present within the hydrocarbon chain. In one embodiment, the stereochemistry of the unsaturation in the long chain is all cis, all trans, or a mixture thereof.

The term "prodrug" as used herein refers to any form of a compound of the disclosure which is administered to a mammal, such as a human, and is chemically converted in vivo, for example, by metabolization, into the active compound of the disclosure. The conversion of the prodrug into the compound is not specifically restricted and includes any chemical and/or physical alteration of the prodrug which occurs after administration, such as for example release of an active part of the prodrug at the site of action. Prodrugs include esters, as well as anhydrides, amides, and carbamates that are hydrolyzed in fluids, such as biological fluids, to produce the compounds of the disclosure.

The term "solvate" as used herein includes, but is not limited to, a molecular or ionic complex of molecules or ions of a solvent with molecules or ions of the compound(s) of the disclosure. A specific example of a solvate is a hydrate, wherein the solvent is water. In an embodiment, hydrates may or may not have solvents other than water on the surface, in the lattice or on the surface and in the lattice of a substance.

The term "therapeutically effective amount" as used herein refers to an amount of a compound of the disclosure sufficient to treat or prevent the condition or disease or one or more of the symptoms of the condition or disease being treated. A "therapeutically effective amount" and/or dosage range for a compound of the disclosure used in the method of treatment of the disclosure may be determined by one of ordinary skill in the art via known criteria including age, weight, and response of the individual patient, and interpreted within the context of the disease being treated and/or prevented.

(II) Compounds of the Disclosure

Catechins, which include epicatechin (EC) (1), epicatechin gallate (ECG) (2), epigallocatechin (EGC) (3) and epigallocatechin gallate (EGCG) (4) and to a lesser extent their epimers (i.e. catechin, catechin gallate, gallocatechin, gallocatechin gallate, respectively), are a widely studied group of compounds found in green tea and have been proposed as functional food ingredients and nutraceuticals for therapeutic use.

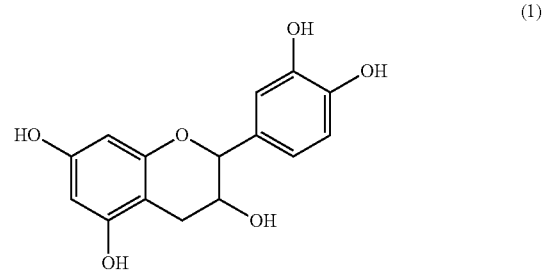

(1)

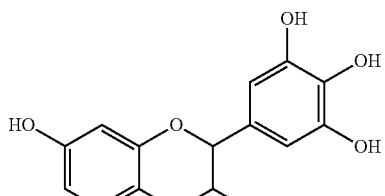

(2)

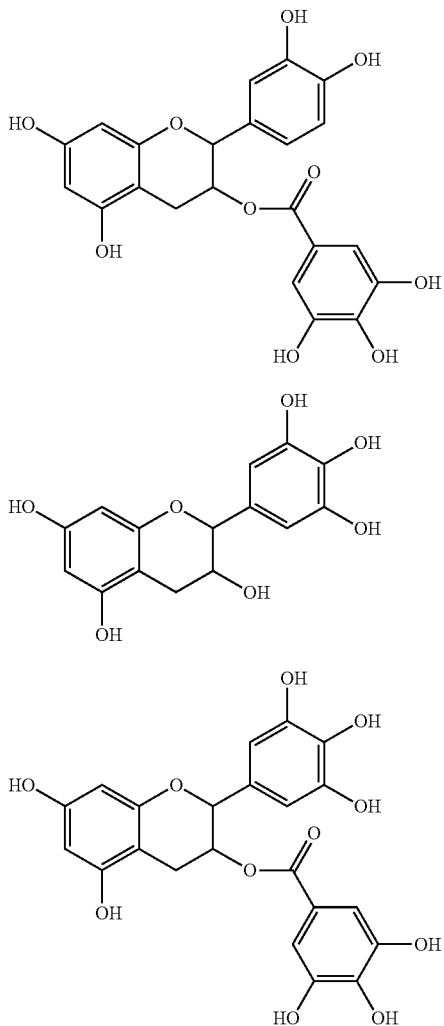

(3)

(4)

However, catechins are hydrophilic possessing poor solubility in lipophilic media. Thus, they render their functional properties or health effects mainly in aqueous environments or water compartments in body tissues. Moreover, the hydrophilicity of catechins, such as EGCG, also hinders their absorption in vivo, resulting in limited uptake by the cells and bioavailability when ingested orally.

It has now been determined that the esterification of catechins, such as EGCG, with fatty acids, such as omega-3 fatty acids, provides a way to increase the lipophilicity of EGCG, leading to expanded applications in more diverse systems (e.g. fats and oils, lipid-based foods and cosmetics as well as most biological systems) and improved cellular absorption and bioefficiency under physiological conditions. In an embodiment, progressive derivatization of catechins, such as EGCG, with fatty acids, such as leading to tetra-esters, show increased lipophilicity (compared to an unsubstituted catechin), and moreover, the higher degree of substitution improves stability against digestion due to the approach of digestive enzymes toward the compound being sterically hindered. Moreover, the derivatization of a catechin, such as EGCG, with a fatty acid, such as an omega-3 fatty acid, results in beneficial effects, for example, in the treatment of cancer (for example, colon cancer).

Accordingly, the administration of fatty acid derivatives of catechins, such as EGCG, leads to increased beneficial effects when fatty acid derivatives of catechins are administered, as opposed to unsubstituted catechins. Accordingly, the fatty acids are converted to their corresponding acyl chlorides and reacted with the hydroxyl groups of the catechins, such as EGCG, to form the fatty acid derivatives. In addition, omega-3 polyunsaturated fatty acids, such as eicospentaenoic (EPA), docosapentaenoic (DPA), docosahexaenoic acid (DHA) and stearidonic acid, originating from marine and/or other sources possess cardioprotective, immuno-enhancing and mental health improving effects.

In an embodiment, the EGCG derivatives synthesized increase the solubility and efficacy of EGCG in lipophilic media, such as fats and lipid based cosmetics, liposome drug delivery systems, cellular environments, etc.

Accordingly, the present disclosure relates to a compound of the formula (I):

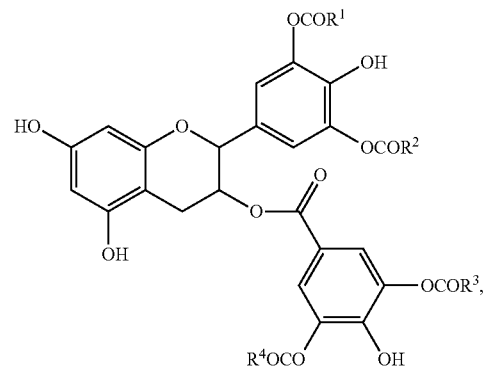

(I)

wherein
$R^1$, $R^2$, $R^3$ and $R^4$ are independently or simultaneously $C_{1-3}$alkyl, $C_{2-3}$alkenyl or an unsaturated or saturated aliphatic moiety of a short, medium- or long-chain fatty acid,
or a pharmaceutically acceptable salt, prodrug, solvate or regio- or stereoisomer thereof.

In another embodiment, the unsaturated or saturated aliphatic moiety of long chain fatty acid contains between 13 and 21 carbon atoms. In another embodiment, the unsaturated or saturated aliphatic moiety of long chain fatty acid contains zero, one, two, three, four, five or six double bonds. In a further embodiment, the unsaturated or saturated aliphatic moiety of long chain fatty acid is selected from the formula (i), (ii), (iii) and (iv)

$$—(CH_2)_{16}CH_3 \qquad (i)$$

$$—(CH_2)_3(CH=CHCH_2)_5CH_3 \qquad (ii)$$

$$—(CH_2)_2(CH=CHCH_2)_6CH_3 \qquad (iii)$$

$$—(CH_2)_5(CH=CHCH_2)_5CH_3 \qquad (iv).$$

In another embodiment, $R^1$, $R^2$, $R^3$ and $R^4$ are propyl.

In another embodiment, $R^1$, $R^2$, $R^3$ and $R^4$ are simultaneously $C_{1-3}$alkyl, $C_{2-3}$alkenyl or an unsaturated or saturated aliphatic moiety of medium- or long-chain fatty acid.

In another embodiment, $R^1$, $R^2$, $R^3$ and $R^4$ independently or simultaneously comprise an unsaturated aliphatic moiety of long chain fatty acid. It has been found that catechins which have been derivatized with unsaturated aliphatic moieties of fatty acid possess an increase in lipophilicity when compared with corresponding unsubstituted catechins. Accordingly, the fatty acid catechin derivatives, for example containing the unsaturated aliphatic moiety of fatty acid, have improved lipophilic properties, which allow the derivatives to be used in lipophilic applications such as in fats and oils and lipid-based food and cosmetics.

In another embodiment, the aliphatic moiety of long chain fatty acid is derived from an omega-3 fatty acid such as, but not limited to, 7,10,13-hexadecatrienoic acid, 9,12,15-octadecatrienoic acid (such as 9Z,12Z,15Z-octadecatrienoic acid), 6,9,12,15-octadecatetraenoic acid, 6Z,9Z,12Z,15Z-octadecatetraenoic acid, 11,14,17-eicosatrienoic acid, 8,11,14,17-eicosatetraenoic acid, 5,8,11,14,17-eicosapentaenoic acid, 7,10,13,16,19-docosapentaenoic acid, 4,7,10,13,16,19-docosahexaenoic acid, 9,12,15,18,21-tetracosapentaenoic acid or 6,9,12,15,18,21-tetracosahexaenoic acid. In another embodiment, the above omega-3 fatty acids have a stereochemistry (of the unsaturation) which is all cis, all trans, or a mixture of cis and trans.

In another embodiment, the aliphatic moiety of long chain fatty acid is derived from an omega-6 fatty acid such as, but not limited to, 9,12-octadecadienoic acid, 6,9,12-octadecatrienoic acid, 6Z,9Z,12Z-octadecatrienoic acid, 11,14-eicosadienoic acid, 8,11,14-eicosatrienoic acid, 5,8,11,14-eicosatetraenoic acid, 13,16-docosadienoic acid, 7,10,13,16-docosatetraenoic acid, or 4,7,10,13,16-docosapentaenoic acid. In another embodiment, where the stereochemistry is not indicated, the above omega-6 fatty acids have a stereochemistry (of the unsaturation) which is all cis, all trans, or a mixture of cis and trans.

In another embodiment, the aliphatic moiety of long chain fatty acid is derived from an omega-9 fatty acid such as, but not limited to, 9-octadecenoic acid, 11-eicosaenoic acid, 5,8,11-eicosatrienoic acid, 13-docosaenoic acid or 15-tetracosaenoic acid. In another embodiment, the above omega-9 fatty acids have a stereochemistry (of the unsaturation) which is all cis, all trans, or a mixture of cis and trans.

In another embodiment, the long chain fatty acid is derived from marine oils or algal oils, or the corresponding hydrolyzed compounds.

In another embodiment of the disclosure, the compound of the formula (I) comprises

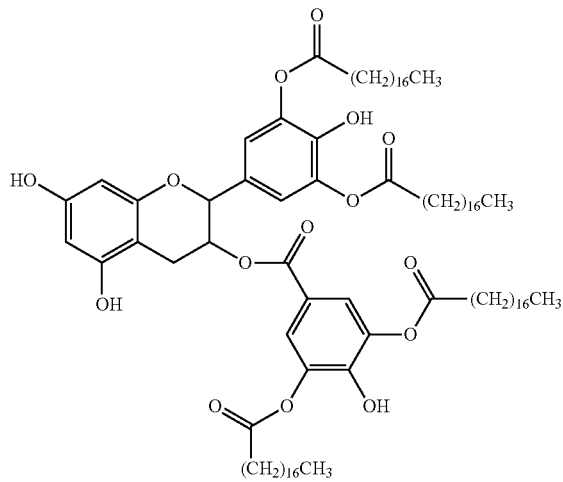

-continued

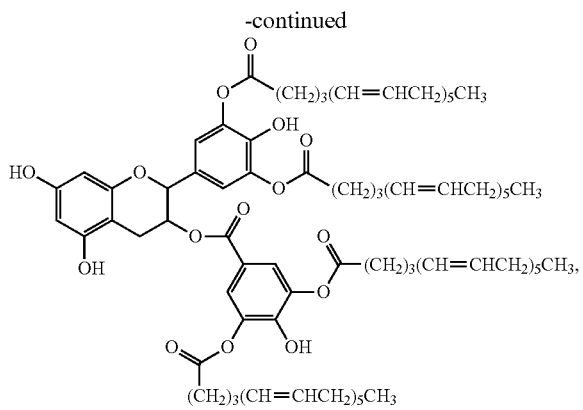

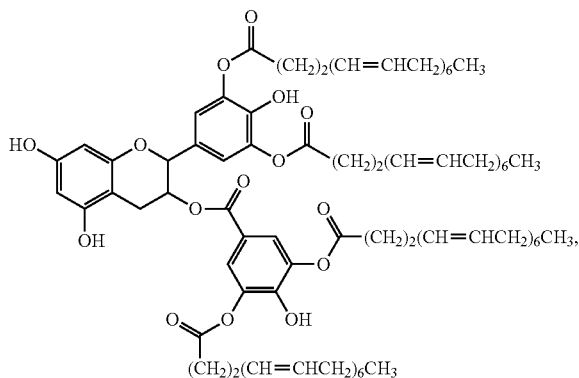

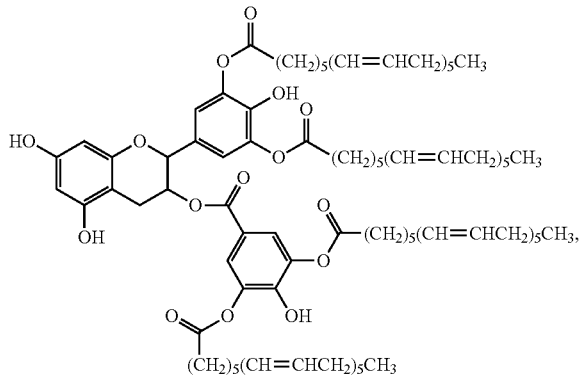

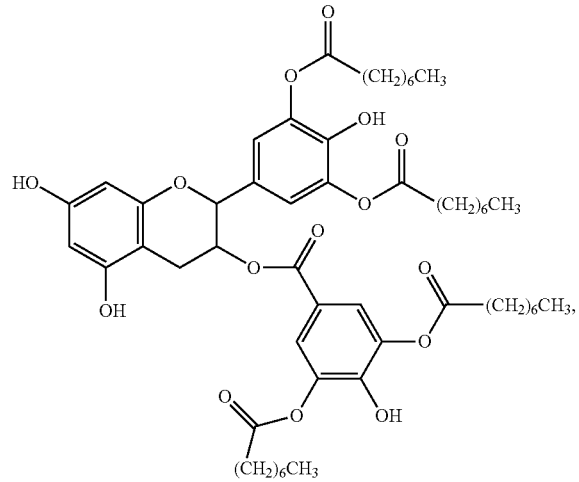

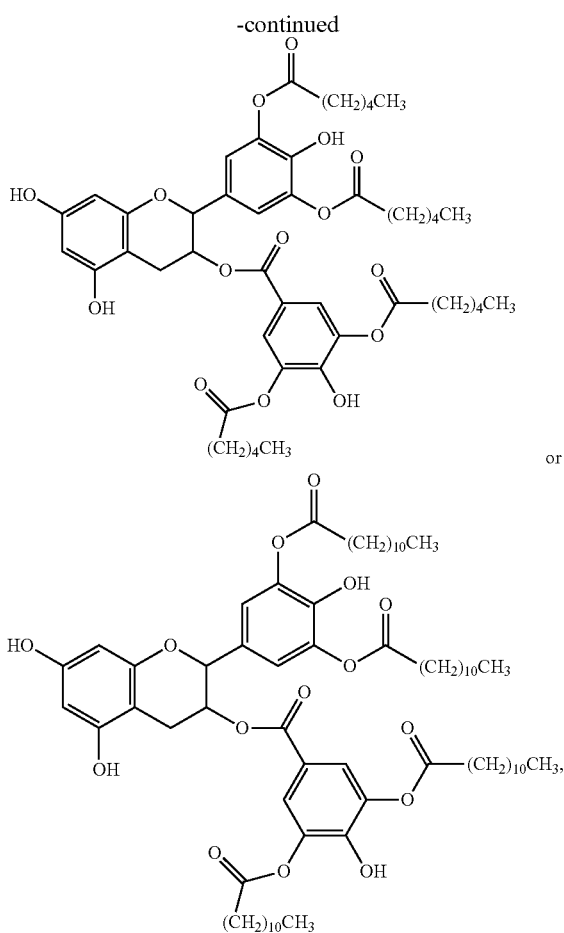

and their isomers thereof.

In another embodiment of the disclosure, there is also included a compound of the formula (2):

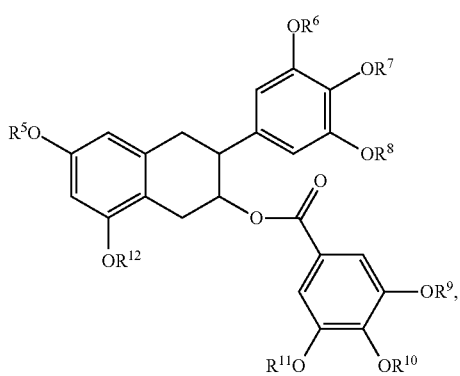

wherein $R^5$-$R^{12}$ are independently or simultaneously H or —C(=O)$R^{13}$, wherein $R^{13}$ is independently or simultaneously $C_{1-3}$alkyl, $C_{2-3}$alkenyl or an unsaturated or saturated aliphatic moiety of a short, medium or long chain fatty acid, or a pharmaceutically acceptable salt, prodrug, solvate or regio- or stereoisomer thereof.

In another embodiment, the compound of formula (2) is a mono-ester, di-ester, tri-ester, tetra-ester, penta-ester, hexa-ester, hepta-ester or octa-ester.

In another embodiment, the unsaturated or saturated aliphatic moiety of long chain fatty acid contains between 13 and 21 carbon atoms. In another embodiment, the unsaturated or saturated aliphatic moiety of long chain fatty acid contains zero, one, two, three, four, five or six double bonds. In a further embodiment, the unsaturated or saturated aliphatic moiety of long chain fatty acid is selected from the formula (i), (ii), (iii) and (iv)

$$—(CH_2)_{16}CH_3 \qquad (i)$$

$$—(CH_2)_3(CH=CHCH_2)_5CH_3 \qquad (ii)$$

$$—(CH_2)_2(CH=CHCH_2)_6CH_3 \qquad (iii)$$

$$—(CH_2)_5(CH=CHCH_2)_5CH_3 \qquad (iv).$$

In another embodiment, $R^5$-$R^{12}$ are simultaneously —C(=O)$R^{13}$, and each $R^{13}$, simultaneously comprises an unsaturated aliphatic moiety of long chain fatty acid.

In another embodiment, $R^5$-$R^{12}$ are simultaneously —C(=O)$R^{13}$, and each $R^{13}$ are simultaneously $C_{1-3}$alkyl, $C_{2-3}$alkenyl or an unsaturated or saturated aliphatic moiety of medium- or long-chain fatty acid.

In another embodiment, the aliphatic moiety of long chain fatty acid is derived from an omega-3 fatty acid such as, but not limited to, 7,10,13-hexadecatrienoic acid, 9,12,15-octadecatrienoic acid, 6,9,12,15-octadecatetraenoic acid, 11,14,17-eicosatrienoic acid, 8,11,14,17-eicosatetraenoic acid, 5,8,11,14,17-eicosapentaenoic acid, 7,10,13,16,19-docosapentaenoic 4,7,10,13,16,19-docosahexaenoic acid, acid, 9,12,15,18,21-tetracosapentaaenoic acid or 6,9,12,15,18,21-tetracosahexaenoic acid. In another embodiment, the above omega-3 fatty acids have a stereochemistry (of the unsaturation) which is all cis, all trans, or a mixture of cis and trans.

In another embodiment, the aliphatic moiety of long chain fatty acid is derived from an omega-6 fatty acid such as, but not limited to, 9,12-octadecadienoic acid, 6,9,12-octadecatrienoic acid, 11,14-eicosadienoic acid, 8,11,14-eicosatrienoic acid, 5,8,11,14-eicosatetraenoic acid, 13,16-docosadienoic acid, 7,10,13,16-docosatetraenoic acid, 4,7,10,13,16-docosapentaenoic acid or 8E,10E,12Z-octadecatrienoic acid. In another embodiment, where the stereochemistry is not indicated, the above omega-6 fatty acids have a stereochemistry (of the unsaturation) which is all cis, all trans, or a mixture of cis and trans.

In another embodiment, the aliphatic moiety of long chain fatty acid is derived from an omega-9 fatty acid such as, but not limited to, 9-octadecaenoic acid, 11-eicosaenoic acid, 5,8,11-eicosatrienoic acid, 13-docosaenoic acid or 15-tetracosaenoic acid. In another embodiment, the above omega-9 fatty acids have a stereochemistry (of the unsaturation) which is all cis, all trans, or a mixture of cis and trans.

In another embodiment, the aliphatic moiety of medium chain fatty acid is derived from caproic acid, caprylic acid, capric acid or lauric acid. In another embodiment, the aliphatic moiety of short chain fatty acid is derived from acetic acid, propionic acid, isobutyric acid, butyric acid, isovaleric acid or valeric acid, optionally butyric acid. In another embodiment, the compound of the formula (2) is EGCG-perbutyrate.

In another embodiment, the aliphatic moiety of long chain fatty acid is derived from marine oils or algal oils, or the corresponding hydrolyzed compounds.

The present disclosure also provides a process for the production of the compounds of the disclosure. In an embodiment, a short, medium- or long-chain fatty acid, for example stearic acid in its free form or as a triacylglycerol, or in crude oils, is converted to its corresponding acyl chloride, using a reagent such as thionyl chloride or oxalyl chloride, to produce the corresponding acyl chloride (in this case, stearoyl chloride). The process is optionally performed in the presence of a base, such as pyridine or triethylamine. In another embodiment, a catechin, for example, EGCG or a mixture of catechins or a crude extract of green tea, is reacted with multiple equivalents of the acyl chloride (stearoyl chloride) to produce the compounds of the disclosure. In another embodiment, catechins are reacted either with a fatty acid in the presence of a dehydrating/condensing agent such as a carbodiimide derivative. In an embodiment, the reactions are carried out in an aprotic solvent or in a solventless manner at 0-60° C. for 2-24 hours. In an embodiment, by manipulating the ratio of the reactants (such as the fatty acid chloride and the catechin), the amount of derivatization of the catechin is altered. For example, one embodiment, by using a small amount of acyl chloride compared to the catechin, the main product is a monoester or diester. As the amount of acyl chloride is increased, the derivatization of catechin will correspondingly increase and generate a triester, tetraester, pentaester, hexaester, heptaester or an octaester.

In another embodiment, the compounds of the formula disclosure are produced in an enzymatic reaction, such that enzymes, for example an esterase, are used to derivatize the catechins with the fatty acids. In an embodiment, esterases such as, but not limited to, chlorogenate esterase or ferulate esterase are used in the enzymatic reaction. These enzymes are derived from *Asp. japonicus* and *Lactobacillus acidophilus*, among others. In an embodiment, in such a reaction, hydroxyl groups on the catechins are esterified with the fatty acids, which can be used in the free form. In an embodiment, to carry out the reaction, an aqueous solution of catechins and a solution of fatty acids, esters, triacylglycerols or their corresponding acyl chlorides thereof, optionally in organic solvents, are first prepared and after adding an enzyme either in powder form or as dissolved in water, the ingredients are left to stand, stirred, shaken or mixed together. The reaction temperature is about 10-60° C., optionally about 30-50° C.

In another embodiment of the disclosure, there is also provided a crude green tea extract containing fatty acid derivatives of epicatechin (EC), epicatechin gallate (ECG), epigallocatechin (EGC) and epigallocatechin gallate (EGCG), in which at least two, optionally three, of the hydroxy groups on the catechins are derivatized with fatty acids.

In another embodiment, the derivatized crude green tea extract comprises compounds of the formula (II), (III), (IV) and (V):

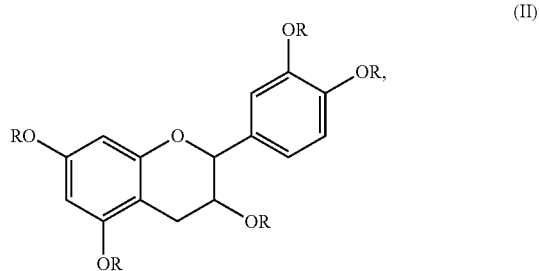

(II)

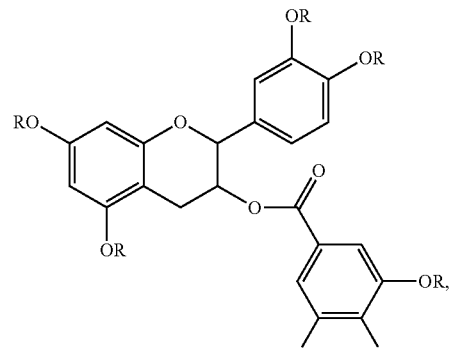

(III)

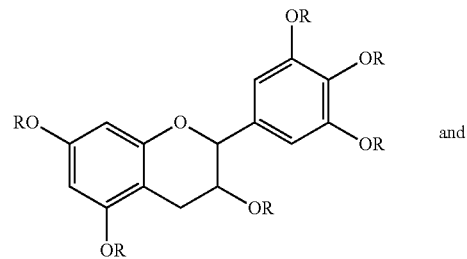

(IV)

and

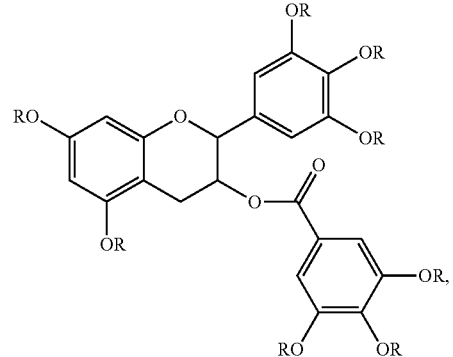

(V)

wherein
each R is independently or simultaneously H or —C(=O)R",
wherein
R" is independently or simultaneously $C_{1-3}$alkyl, $C_{2-3}$alkenyl or an unsaturated or saturated aliphatic moiety of medium- or long-chain fatty acid,
or a pharmaceutically acceptable salt, prodrug, solvate or regio- or stereoisomer thereof,
and wherein in each compound of the formula (II), (III), (IV) and (V), at least two R groups are substituted with —C(=O)R".

In another embodiment, the compound of formulae (II), (III), (IV) and/or (V) is a mono-ester, di-ester, tri-ester, tetraester, penta-ester, hexa-ester, hepta-ester or octa-ester.

In another embodiment, the unsaturated or saturated aliphatic moiety of long chain fatty acid contains between 13 and 21 carbon atoms. In another embodiment, the unsaturated or saturated aliphatic moiety of long chain fatty acid contains zero, one, two, three, four, five or six double bonds. In a further embodiment, the unsaturated or saturated aliphatic moiety of long chain fatty acid is selected from the formula (i), (ii), (iii) and (iv)

—(CH$_2$)$_{16}$CH$_3$      (i)

—(CH$_2$)$_3$(CH=CHCH$_2$)$_5$CH$_3$      (ii)

—(CH$_2$)$_2$(CH=CHCH$_2$)$_6$CH$_3$   (iii)

—(CH$_2$)$_5$(CH=CHCH$_2$)$_5$CH$_3$   (iv).

In another embodiment, each R independently or simultaneously comprise an unsaturated aliphatic moiety of long chain fatty acid.

In another embodiment, each R is simultaneously —C(=O)R", and each R" is simultaneously C$_{1-3}$alkyl, C$_{2-3}$alkenyl or an unsaturated or saturated aliphatic moiety of medium or long chain fatty acid.

In another embodiment, the aliphatic moiety of long chain fatty acid is derived from an omega-3 fatty acid such as, but not limited to, 7,10,13-hexadecatrienoic acid, 9,12,15-octadecatrienoic acid, 6,9,12,15-octadecatetraenoic acid, 11,14,17-eicosatrienoic acid, 8,11,14,17-eicosatetraenoic acid, 5,8,11,14,17-eicosapentaenoic acid, 7,10,13,16,19-docosapentaenoic acid, 4,7,10,13,16,19-docosahexaenoic acid, 9,12,15,18,21-tetracosapentaenoic acid or 6,9,12,15,18,21-tetracosahexasenoic acid. In another embodiment, the above omega-3 fatty acids have a stereochemistry (of the unsaturation) which is all cis (Z), all trans (E), or a mixture of cis and trans.

In another embodiment, the aliphatic moiety of long chain fatty acid is derived from an omega-6 fatty acid such as, but not limited to, 9,12-octadecadienoic acid, 6,9,12-octadecatrienoic acid, 11,14-eicosadienoic acid, 8,11,14-eicosatrienoic acid, 5,8,11,14-eicosatetraenoic acid, 13,16-docosadienoic acid, 7,10,13,16-docosatetraenoic acid, 4,7,10,13,16-docosapentaenoic acid or 8E,10E,12Z-octadecatrienoic acid. In another embodiment, where the stereochemistry is not indicated, the above omega-6 fatty acids have a stereochemistry (of the unsaturation) which is all cis, all trans, or a mixture of cis and trans.

In another embodiment, the aliphatic moiety of long chain fatty acid is derived from an omega-9 fatty acid such as, but not limited to, 9-octadecaenoic acid, 11-eicosaenoic acid, 5,8,11-eicosatrienoic acid, 13-docosaenoic acid or 15-tetracosaenoic acid. In another embodiment, the above omega-9 fatty acids have a stereochemistry (of the unsaturation) which is all cis, all trans, or a mixture of cis and trans.

In another embodiment, the aliphatic moiety of medium chain fatty acid is derived from caproic acid, caprylic acid, capric acid or lauric acid. In another embodiment, the aliphatic moiety of short chain fatty acid is derived from acetic acid, propionic acid, isobutyric acid, butyric acid, isovaleric acid or valeric acid, optionally butyric acid. In another embodiment, the compound of the formula (2) is EGCG-perbutyrate.

In another embodiment, the aliphatic moiety of long chain fatty acid is derived from marine oils or algal oils, or the corresponding hydrolyzed compounds.

In another embodiment, the aliphatic moiety of medium chain fatty acid is derived from caproic acid, caprylic acid, capric acid or lauric acid. In another embodiment, the aliphatic moiety of short chain fatty acid is derived from acetic acid, propionic acid, isobutyric acid, butyric acid, isovaleric acid or valeric acid.

(III) Methods of Use

In an embodiment of the disclosure, there is provided a method for the treatment of atherosclerosis in a mammal comprising administering to the mammal a therapeutically effective amount of a compound of the disclosure as defined above, or a green tea crude extract derivatized with a fatty acid(s) as described above. In another embodiment, there is also provided a method for reducing the oxidation of LDL-cholesterol comprising contacting the LDL-cholesterol with a compound of the disclosure as defined above, or a green tea crude extract derivatized with a fatty acid(s) as described above. In another embodiment, there is also provided a method of reducing the oxidation of LDL-cholesterol in a mammal, such as a human, comprising administering to the mammal a therapeutically effective amount of a compound of the disclosure as defined above, or a green tea crude extract derivatized with a fatty acid(s) as described above.

In an embodiment of the disclosure, there is further provided a method for the treatment of inflammation in a mammal comprising administering to the mammal a therapeutically effective amount of a compound of the disclosure as defined above, or a green tea crude extract derivatized with a fatty acid(s) as described above. In another embodiment, there is also included a method for the inhibition of cyclooxygenase-2 (COX-2), inducible nitric oxide NO synthase (iNOS) or lipopolysaccharide (LPS)-induced NO production comprising contacting an effective amount of a compound of the disclosure with COX-2, iNOS or LPS. In another embodiment, there is also included a method for the inhibition of COX-2, iNOS or LPS-induced NO production in a mammal, such as a human, comprising administering to the mammal a therapeutically effective amount of a compound of the disclosure as defined above, or a green tea crude extract derivatized with a fatty acid(s) as described above.

In an embodiment of the disclosure, there is also provided a method for the treatment of a viral infection in a mammal comprising administering to the mammal a therapeutically effective amount of a compound of the disclosure as defined above, or a green tea crude extract derivatized with a fatty acid(s) as described above. In another embodiment, the viral infection comprises a hepatitis infection, optionally a hepatitis C infection. In another embodiment, there is also provided a method for inhibiting viral proteases or α-glucosidases, such as a protease derived from a hepatitis C virus, comprising contacting the protease or α-glucosidase for HIV viral infectivity with an effective amount of a compound of the disclosure as defined above, or a green tea crude extract derivatized with a fatty acid(s) as described above.

In another embodiment, there is provided a method for the inhibition of cell proliferation in a mammal comprising administering to the mammal a therapeutically effective amount of a compound of the disclosure as defined above, or a green tea crude extract derivatized with a fatty acid(s) as described above. In another embodiment of the disclosure, there is provided a method for the treatment of cancer in a mammal comprising administering to the mammal a therapeutically effective amount of a compound of the disclosure as defined above, or a green tea crude extract derivatized with a fatty acid(s) as described above. In another embodiment, the cancer comprises colon cancer.

In another embodiment, there is also provided a method for the inhibition of radical (such as hydroxyl or peroxyl radicals, optionally produced by UV radiation) induced DNA-scission which optionally leads to mutagenesis or carcinogenesis in a mammal, such as a human, the method comprising administering a therapeutically effective amount of a compound of the disclosure as defined above, or a green tea crude extract derivatized with a fatty acid(s) as described above, to the mammal.

In another embodiment, there is also provided a method for the inhibition of ultraviolet (UV)-induced photo-oxidation, the method comprising administering a therapeutically effective amount of a compound of the disclosure as defined above, or a green tea crude extract derivatized with a fatty acid(s) as described above, to the mammal.

In another embodiment, there is provided a method for the preservation of a foodstuff or model food by the application to the foodstuff of a compound of the disclosure as defined above, or a green tea crude extract derivatized with a fatty acid(s) as described above, wherein the compounds inhibit the oxidation of unsaturated fatty acids, and therefore, inhibit the decomposition of the food products.

In another embodiment of the disclosure, there is also provided a use of a therapeutically effective amount of a compound of the disclosure as defined above, or a green tea crude extract derivatized with a fatty acid(s) as described above, for the treatment of atherosclerosis in a mammal.

In a further embodiment of the disclosure, there is a provided a use of a therapeutically effective amount of a compound of the disclosure as defined above, or a green tea crude extract derivatized with a fatty acid(s) as described above, for the treatment of inflammation in a mammal.

In an embodiment of the disclosure, there is also provided a use of a therapeutically effective amount of a compound of the disclosure as defined above, or a green tea crude extract derivatized with a fatty acid(s) as described above, for the treatment of a viral infection in a mammal. In another embodiment, the viral infection comprises a hepatitis infection, optionally a hepatitis C infection, and HIV infection.

In another embodiment of the disclosure, there is provided a use of a therapeutically effective amount of a compound of the disclosure as defined above, or a green tea crude extract derivatized with a fatty acid(s) as described above, for the inhibition of cell proliferation in a mammal. In another embodiment of the disclosure, there is provided a use of a therapeutically effective amount of a compound of the disclosure as defined above, or a green tea crude extract derivatized with a fatty acid(s) as described above, for the treatment of cancer in a mammal. In another embodiment, the cancer comprises colon cancer.

In another embodiment of the disclosure, as a result of the physiological activity of the compounds of the disclosure as defined above, or a green tea crude extract derivatized with a fatty acid(s) as described above, the compounds are useful as nutritional and/or cosmetic supplements (for use in skin care). In another embodiment, the compounds of the disclosure as defined above, or a green tea crude extract derivatized with a fatty acid(s) as described above, are useful as nutraceutical and/or pharmaceutical agents. In another embodiment, the disclosure includes a pharmaceutical composition comprising one or more compounds of the disclosure as defined above, or a green tea crude extract derivatized with a fatty acid(s) as described above and a pharmaceutically acceptable carrier. In another embodiment, the compounds of the disclosure as defined above, or a green tea crude extract derivatized with a fatty acid(s) as described above, are useful as a functional food ingredient, natural health product or dietary supplement.

In another embodiment, the compounds of the disclosure as defined above, or a green tea crude extract derivatized with a fatty acid(s) as described above, are loaded into liposomes for administration to a mammal, such as a human. Liposomes provide a way to administer agents (such as a pharmaceutical agent) to a mammal, such as in oral administration, which otherwise are degraded by the harsh conditions in the gastrointestinal system of a mammal. Liposomes generally comprise a lipid bilayer, which surrounds a core containing an agent. In an embodiment, as a result of the liposomes being lipid based, it is sometimes difficult to include agents, such as EGCG, which are hydrophilic. Accordingly, in an embodiment, as a result of the compounds of the disclosure as defined above, or a green tea crude extract derivatized with a fatty acid(s) as described above, being more lipophilic than EGCG, the compounds of the disclosure as defined above, or a green tea crude extract derivatized with a fatty acid(s) as described above, are loaded into liposomes for administration to a mammal.

In another embodiment, the compounds of the disclosure as defined above, or a green tea crude extract derivatized with a fatty acid(s) as described above, are used for food preservation. In an embodiment, the decomposition of lipid containing food products, proceeds by the oxidation of unsaturated fatty acids, wherein oxygen reacts with the unsaturated fatty acids. In an embodiment, the compounds of the disclosure as defined above, or a green tea crude extract derivatized with a fatty acid(s) as described above, inhibit the oxidation of the unsaturated fatty acids, and therefore inhibit the decomposition of the food products.

Pharmaceutically acceptable salts of the compounds of the disclosure as defined above, or a green tea crude extract derivatized with a fatty acid(s) as described above, are also included in the disclosure, and are well-known in the art. The salts can be prepared in situ during the final isolation of the compounds of the disclosure as defined above, or a green tea crude extract derivatized with a fatty acid(s) as described above, or separately by reacting the free acid function with a suitable base. Representative alkali or alkaline earth metal salts include sodium, lithium, potassium, calcium, magnesium, and the like, as well as nontoxic ammonium, quaternary ammonium, and amine cations including, but not limited to, ammonium, tetramethylammonium, and tetraethylammonium.

In another embodiment, the compounds of the disclosure as defined above, or a green tea crude extract derivatized with a fatty acid(s) as described above, are formulated into pharmaceutical compositions with a pharmaceutically acceptable excipients.

In an embodiment, the compounds of the disclosure as defined above, or a green tea crude extract derivatized with a fatty acid(s) as described above, are administered in a standard manner for the treatment of diseases, for example orally, parenterally, sub-lingually, dermally, intranasally, transdermally, rectally, via inhalation or via buccal administration, and optionally include pharmaceutically acceptable excipients.

In another embodiment, the compounds of the disclosure as defined above, or a green tea crude extract derivatized with a fatty acid(s) as described above, when given orally are formulated as syrups, tablets, capsules and lozenges. A syrup formulation will generally consist of a suspension or solution of the compound or salt in a liquid carrier for example, ethanol, edible oils, such as peanut oil or olive oil, glycerine or water with a flavoring or colouring agent. Where the capsules are in the form of a tablet, any pharmaceutical carrier routinely used for preparing solid formulations may be used. Examples of such carriers include magnesium stearate, terra alba, talc, gelatin, acacia, stearic acid, starch, modified starch and products thereof lactose and sucrose as well as protein-based materials.

In an embodiment, the compounds of the disclosure as defined above, or a green tea crude extract derivatized with a fatty acid(s) as described above, are delivered by ingestion, subcutaneous injection, intravenous injection, inhalation, intraocular/periocular injection or nasal inhalation.

Typical parenteral compositions include a solution or suspension of a compound or derivative in a sterile aqueous or non-aqueous carrier optionally containing a parenterally acceptable oil, for example polyethylene glycol, polyvinylpyrrolidone, lecithin, peanut oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of the disclosure as defined above, or a green tea crude extract derivatized with a fatty acid(s) as described above, or a pharmaceutically acceptable derivative thereof which is active when administered in this way, with a binding and/or lubricating agent, for example polymeric glycols, gelatins, cocoabutter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

The following non-limiting examples are illustrative of the present disclosure:

EXAMPLES

Materials and Methods

Example 1

General Procedure for the Synthesis of Fatty Acid Derivatives of EGCG

Long-chain fatty acids, namely EPA and DHA, used for acylation were prepared from EPA ethyl ester and DHA single cell oil (DHASCO, containing 40% DHA), respectively. EPA was obtained following saponification and DHA was prepared by saponification followed by a urea complexation process as described by Wanasundara and Shahidi (1999). The purity of fatty acids was confirmed by GC-MS. EPA, DHA and DPA were then converted to their corresponding acyl chlorides by reacting with thionyl chloride. Butyroyl, caproyl, capryloyl, lauroyl and stearoyl chlorides were obtained from a commercial source and used as such. Esterification of EGCG was carried out with acyl chlorides (stearoyl, eicosapentaenoyl, docosahexaenoyl, docosapentaenoyl, caproyl, capryloyl and lauroyl chloride) at a mole ratio of 1:1. Acyl chloride was added dropwise to EGCG dissolved in ethyl acetate, and the reaction was catalyzed by pyridine, which removed the released HCl from the medium. The mixture was then heated in an oil bath at 50° C. and under a nitrogen blanket with constant stirring. The reaction mixture upon completion of the esterification was cooled to ambient temperature and filtered. The filtrate was then washed 3 times with distilled water (60° C.), and the ethyl acetate layer was collected and passed through a cone of anhydrous sodium sulphate. The dry powder of crude products containing a mixture of EGCG esters (at different degrees of substitution) was obtained by removing the solvent, using a rotary evaporator. Perbutyrated EGCG (EGCG-octabutyrate) was prepared in a similar manner but with an excess of butyroyl chloride.

The composition of reaction mixture was determined by reversed phase HPLC-MS, using an Agilent 1100 HPLC unit (Agilent Technologies, Palo Alto, Calif.) with a UV-diode array detector (UV-DAD). Separation was achieved on a C-18 column (Agilent) by gradient elution with methanol/water mobile phase (95/5-100/0 from 0-30 min) and fractions were detected at 280 nm. LC flow was further analyzed on-line by the MS detector system (LC-MSD-Trap-SL, Agilent) with APCI (atmospheric pressure chemical ionization) at positive mode for identification of each fraction.

In order to obtain individual EGCG derivatives for subsequent structure elucidation and bioactivity evaluation, the crude products of EGCG esters were purified by flash column chromatography. EGCG esters were eluted on a silica column with a gradient of hexane/ethyl acetate/formic acid (90/10/2-50/50/2). Fractions corresponding to each band were collected and solvents removed using a rotary evaporator. The identity of each fraction was established by HPLC-MS as described above. The predominant fractions of EGCG esters with stearic acid (SA), EPA, DHA, were analyzed for their specific structures and evaluated for their bioactivities. The compounds identified may or may not include isomer forms of those specified.

$^1$H and $^{13}$C NMR analyses were carried out for selected purified EGCG esters in order to identify their molecular structures, i.e. the location of fatty acid incorporation in the EGCG molecule. The $^1$H and $^{13}$C spectra were recorded on a Bruker Avance 500 MHz NMR spectrometer (Bruker Biospin Co., Billerica, Mass.) operating at 500.13 and 125.77 MHz, respectively. The samples were dissolved in dimethyl sulphoxide (DMSO)-d6 containing TMS as internal standard. Signal processing and interpretation were performed with the softwares Topspin 1.3 (Bruker Biospin Co., Billerica, Mass.) and MestRe Nova (Mestrelab Research SL, Santiago De Compostela, Spain) and structure elucidation was accomplished by comparing the chemical shifts of EGCG derivatives with that of the EGCG parent molecule. The EGCG esters have the following structures (1a-1g).

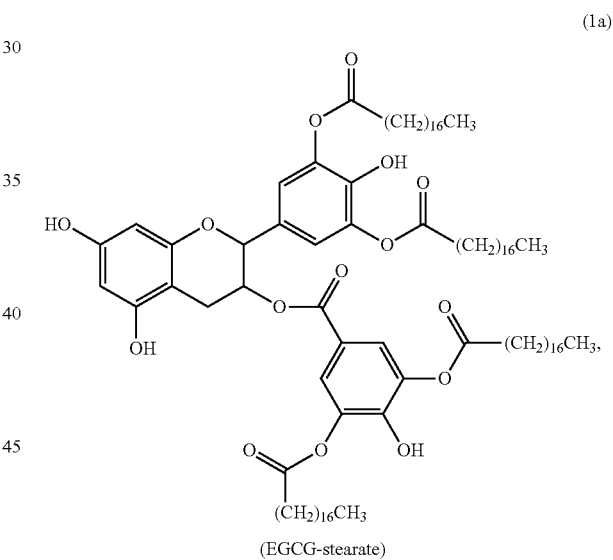

(1a)

(EGCG-stearate)

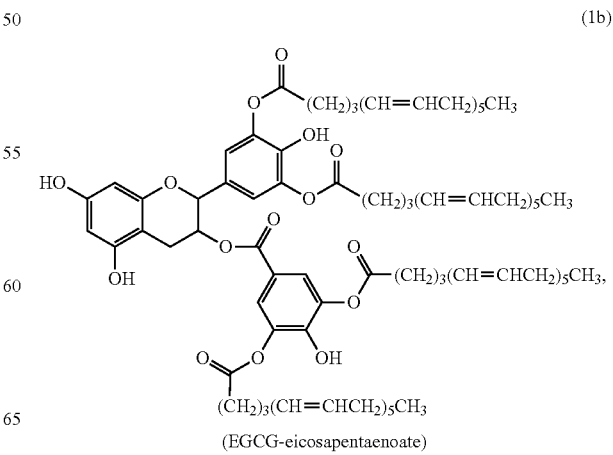

(1b)

(EGCG-eicosapentaenoate)

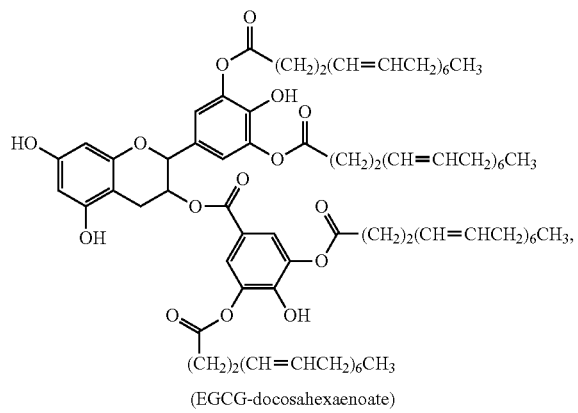
(EGCG-docosahexaenoate)

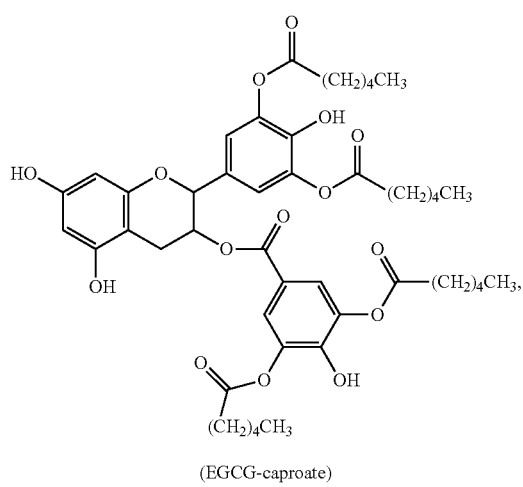
(EGCG-caproate)

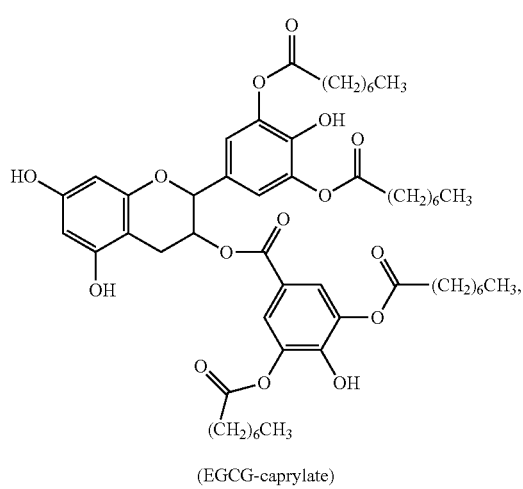
(EGCG-caprylate)

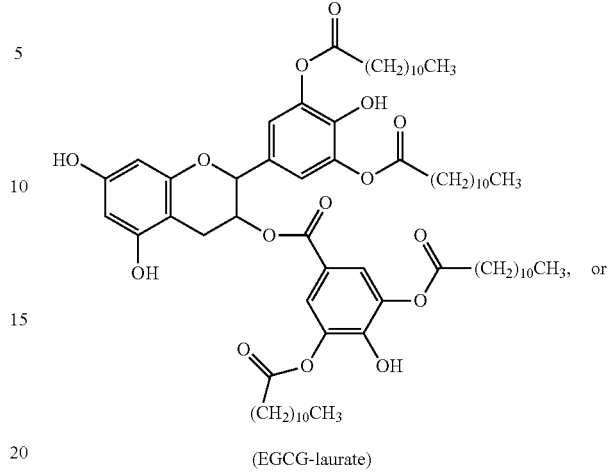
(EGCG-laurate)

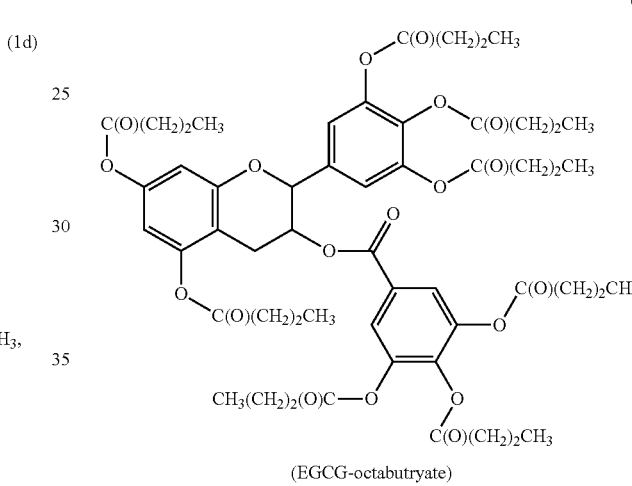
(EGCG-octabutryate)

Discussion

Polyesters of EGCG with high degrees of substitution (DS) (≥4) were formed during acylation under the conditions employed. The composition of the reaction mixture varied depending on the ratio of the starting materials (EGCG/fatty acid); esters with higher DS (7-8) were produced at lower ratios of EGCG/fatty acid (<1). The antioxidant activity of the derivatives is preserved since hydroxyl groups are only partially acylated. Pentaesters were produced at a highest level in the EGCG-SA crude product (36.7%) followed by EGCG-EPA (18.9%) and EGCG-DHA (5.33%), whose fatty acids were less effective in approaching the acyl acceptor and packing in the synthesized molecules.

Example 2

Lipophilicity of EGCG and Fatty Acid Derivatives 1a-1c

Lipophilicity of the identified EGCG derivatives was determined as octanol-water partition coefficient (P) by a shake flask method. Briefly, a flask containing a mixture of octanol (100 ml) and deionized water (100 ml) was shaken in a shaking waterbath at room temperature (22° C.) for 24 hours. The content was then allowed to stand for 24 hours for separation into two phases. Test compounds (0.2 μmol) were dissolved in 5 ml of the upper phase (pre-saturated octanol), and the absorbance ($A_0$) was read at 280 nm. A blank with no sample was prepared. Five milliliters of the bottom phase (pre-saturated water) were added afterwards, and the mixtures were vortexed for 1 min and allowed to stand for 24 hours for separation. Absorbance ($A_x$) of the upper phase in the vials was measured and octanol-water partition coefficient (P) calculated using the following equation: $P=\log A_x/(A_0-A_x)$, where blank-corrected absorbance was used.

Discussion

The lipophilicity values are shown in Table 1, wherein the lipophilicity was determined to be in the order of compound 1a>1c≥1b>EGCG.

As the degree of substitution increases, the lipophilicity increases while hydrolysis by lipolytic enzymes is limited due to steric hindrance, hence higher membrane permeability and metabolic stability of the esters. The enhanced lipophilicity of EGCG derivatives leads to improved incorporation into the lipid bilayers of cell membrane and hence better bioavailability in the body as well as greater potential in liposome-based drug delivery.

Example 3

Antioxidant Activity of EGCG and Fatty Acid Derivatives 1a-1c by In Vitro Chemical Assays (3a) ORAC An ORAC (Oxygen Radical Absorbance Capacity) assay was carried out using a Fluostar Optima plate reader (BMG Labtech, Durham, N.C.) equipped with an incubator and two injector pumps. A modified method for lipophilic antioxidants was followed, in which randomly methylated cyclodextrin (RMCD) was used as water solubility enhancer, as described by Huang et al, *J. Agric. Food Chem.*, 2002, 50, 1815-1821. Trolox standards (6.25-50 µM) and samples (0.25 µM) were dissolved in acetone/water (1:1, v/v) containing 7% RMCD. Fluorescein and MPH [2,2'-azobis(2-aminopropane) dihydrochloride] were used as the probe and radical generator, respectively. Twenty microliters of trolox standard or test compound solutions (7% RMCD used as a control) were added into each well of a 96-well black microplate, followed by addition of fluorescein. The plate was incubated at 37° C. for 15 min and then AAPH in buffer was injected into the wells. The conditions used were as follows: 0.3 s position delay, 8 s orbital shaking before each cycle with 4 mm width, 210 s cycle time, and 25 cycles. Fluorescence was measured at an excitation wavelength of 485 nm and emission of 520 nm. A standard curve was plotted and ORAC values for test compounds were obtained as mol of trolox equivalents (TE) per mol of test compound.

(3b) Reducing Power

The reducing power of EGCG and its derivatives (compounds 1a-1c) was determined according to Oyaizu (1986). One milliliter of test compounds (1 mM in 95% ethanol) was mixed with 2.5 ml of phosphate buffer solution (PBS, 0.2 M, pH 6.6) and 2.5 ml of a 1% solution of potassium ferricyanide, $K_3Fe(CN)_6$. The mixture was incubated at 50° C. for 20 min. A portion of (2.5 ml) of trichloroacetic acid (TCA, 10%) was added to the mixture, and the content was centrifuged at 770×g for 10 min. An aliquot (2.5 ml) of the supernatant was transferred to a tube containing 2.5 ml of distilled water and 0.5 ml of ferric chloride $FeCl_3$ (0.1%). The content was mixed well and the absorbance was recorded at 700 nm. Higher absorbance of the reaction mixture indicates greater reducing power. Ascorbic acid (1-6 mM in 95% ethanol) was used as a standard.

(3c) Metal Chelation

The metal chelation capacity was measured following a procedure by Decker E. A. et al., *J. Agric. Food Chem.*, (1990), 38, pp. 674-677 with modifications. Ethanolic solutions of test compounds (0.2 ml, 1 mM) were mixed well with 1.74 ml of ethanol and 0.02 ml of ferrous chloride ($FeCl_2$, 2 mM). To the mixture 0.04 ml of ferrozine (5 mM) was added, and the reaction mixture was allowed to stand for 10 min for colour development. The absorbance was measured afterwards at 562 nm. A blank without ferrozine was run for each compound, since the antioxidant-$Fe^{2+}$ complex gives a colour that might interfere with the absorbance reading. Metal chelation capacity was calculated using the following equation:

$$\% \text{ chelation} = [1-(Abs._{sample}-Abs._{blank})/Abs._{control}] \times 100$$

where, control was devoid of test compounds, while blank contained no ferrozine.

(3d) DPPH

Antioxidant activity of the lipophilic EGCG derivatives was ALSO evaluated as DPPH (1,1-diphenyl-2-picrylhydrazyl) radical scavenging capacity using EGCG as the reference. DPPH scavenging capacity of test compounds was determined by EPR (electron paramagnetic resonance) according to Madhujith and Shahidi (16) with slight modifications. Trolox standards (50-300 µM) and test compounds (25 µM) were dissolved in ethanol, to which 2 ml of ethanolic DPPH solution (0.18 mM) were added. Contents were mixed well and injected to the sample cavity of a Bruker e-scan EPR food analyzer (Bruker Biospin Co. Billerica, Mass.) through capillary tubing. The spectrum was recorded after 1 min. The operating parameters for EPR were as follows: 1.86 G modulation amplitude, 2.621 s sweep time, 8 scans, 100.000 G sweep width, 3495 G center field, 5.12 ms time constant, 9.795 GHz microwave frequency, and 86 kHz modulation frequency. Reduction of DPPH radical concentration in the presence of test compounds was monitored by change in the corresponding signal intensity. DPPH radical scavenging capacity (%) was calculated using the following equation:

$$\% \text{ scavenging} = 100 \times (1-\text{signal intensity}_{sample}/\text{Signal intensity}_{control})$$

where, control contained no test compounds or trolox. A standard curve was constructed and DPPH scavenging capacities for test compounds were expressed as trolox equivalents (TE).

Discussion

As seen in Table 2, the results showed that the peroxyl radicals generated by AAPH were scavenged by 1a-1c to a greater extent than by the reference antioxidant trolox. The ORAC values of 1a-1c were higher than that of EGCG, indicating their greater hydrogen atom donating ability under the test conditions employed.

FIG. 1 shows the EPR spectra of DPPH radical as affected by the test antioxidants. The presence of test compounds significantly decreased the resonance signal intensity, indicating the scavenging effect of 1a-1c against DPPH radical. When comparing their radical scavenging capacity, compound 1a showed the highest capacity as trolox equivalents, followed by compounds 1c and 1b (as seen in Table 2). All derivatives displayed a higher scavenging activity against DPPH than EGCG itself. The radical scavenging capacity of EGCG was significantly enhanced by the esterification process and incorporation of the fatty acids, which was attributed to the increased lipophilicity and hence greater accessibility/affinity of the derivatives to the lipophilic DPPH radical than the parent EGCG molecule.

The ORAC values of the derivatives (1a-1c) were higher than that of the parent EGCG molecule, indicating their greater hydrogen atom donating ability under the test conditions. The substituents on the phenyl ring play a role in the efficacy of phenolic antioxidant via both electronic and steric effects. Electron donating groups at the ortho and para positions are able to lower the activation energy for hydrogen abstraction and thus enhancing the hydrogen donating capability of the antioxidant. The substitution also hinders the formation of the moderately strong hydrogen bonding of the adjacent hydroxyl groups in the EGCG molecule. These intramolecular hydrogen bonds contribute to the stabilization of the molecule and increased bond dissociation enthalpy (BDE) of the O—H bond, i.e. resistance of the hydrogen atom to dissociation. Without being bound by theory, ortho-substitution of EGCG results in enhanced hydrogen atom donating capacity by reducing intramolecular hydrogen bonds and BDE.

The reducing power of EGCG and its derivatives (1a-1c) was measured as $Fe^{3+}$—$Fe^{2+}$ transformation mediated by the test compounds and expressed as ascorbic acid (a known reducing agent) equivalents. The results showed that EGCG derivatives (compounds 1a-1c) exhibited greater reducing power than ascorbic acid by 2-13 fold. EGCG had the highest reducing power. EGCG derivatives with enhanced lipophilicity have poor solubility in aqueous media and hence compromised activity under the hydrophilic test environment.

EGCG and its derivatives exhibited ferrous ion chelation activity, ranging from 8 to 35%. The highest chelation activity was found for compound 1b, followed by compound 1c. Without being bound by theory, the metal chelation capability found for EGCG-PUFA esters is possibly due to steric changes resulting from the bent structure of the PUFA chain that favours the stability of the antioxidant-$Fe^{2+}$ complex.

Example 4

Antioxidant Activity of EGCG and Fatty Acid Derivatives 1a-1c in Food Model Systems (4a) Bulk Oil System One milliliter of EGCG and its derivatives dissolved in ethanol (1 μmol/ml) was transferred into a reaction vessel, followed by evaporation of the solvent to dryness under a stream of nitrogen. To each vessel (an empty vessel was used as control) 3 g of stripped corn oil (devoid of endogenous antioxidants) were added. The evaluation was carried out under accelerated oxidation in a Rancimat (Metrohm Model 743, Herisau, Switzerland) conditions at 100° C. with an air flow rate of 20 l/h. Lipid oxidation in the absence and presence of test compounds was monitored by changes in electrical conductivity, arising from the formation of volatile oxidation products. The induction periods (IP, time to reach a sudden increase in oxidation rate) were recorded. The longer the IP, the greater the oxidative stability of the oil and hence the higher was the antioxidant potential of the compounds involved. Antioxidant activity was interpreted as protection factor (PF), which was calculated as follow.

$$PF = IP_{sample}/IP_{control}$$

where, $IP_{sample}$ and $IP_{control}$ represent induction periods for the oil with and without test compounds, respectively.

Discussion

Antioxidant activity of 1a in bulk oil was measured as protection against lipid oxidation in a stripped corn oil model system by a well-established Rancimat method. As seen in Table 3, 1a (EGCG stearate) showed higher antioxidant activity than EGCG. Compounds 1b and 1c acted as antioxidants (PF>1) at the lowest concentration, (4b) Oil/Water Emulsion (β-carotene/linoleate) and Meat (Pork) Model System Ten milligrams of β-carotene were dissolved in 10 ml of chloroform. A 1.2 ml portion of this solution was transferred into a round-bottom flask containing 40 mg of linoleic acid and 400 mg of Tween 40. A blank without β-carotene was also prepared (40 mg of linoleic acid+400 mg of Tween 40). After removal of chloroform under a nitrogen stream, 100 ml of oxygenated distilled water were added to the flask and the mixture was stirred vigorously. Aliquots (4.5 ml) of the above emulsion were transferred into a series of tubes containing 0.5 ml of test compounds (1 mM in ethanol) or ethanol as control. A mixture of blank (without β-carotene) was prepared for each sample. The tubes were vortexed and the zero time absorbance was read immediately at 470 nm. The tubes are kept in a water bath at 50° C. with gentle shaking, and measurement of absorbance was continued over a 105-min period at intervals of 15 min. Blank-corrected absorbance was obtained and plotted against time for kinetic curve of β-carotene bleaching. Antioxidant activity (AA) of test compounds in protecting β-carotene/linoleic acid oxidation was calculated using the following equation.

$$AA\% = [1-(A_0-A_t)/(A_0^\circ-A_t^\circ)] \times 100$$

where, $A_0$ and $A_t$ are corrected absorbance values for test samples measured at zero time and after incubation, respectively; while $A_0^\circ$ and $A_t^\circ$ are corrected absorbance values for control at zero time and after incubation, respectively.

Fresh ground pork (40 g) was mixed with deionized water (10 g) in a Mason jar. Samples and reference antioxidant compound (BHA) dissolved in ethanol were added to meat at a level of 80 μmol/kg. A control without any antioxidant was also prepared. The content was thoroughly mixed and cooked at 80° C. in a thermostated water bath for 40 min with intermittent stirring. The cooked meat was cooled to room temperature and homogenized with a Polytron PT 3000 (Brinkmann Instruments, Rexdale, ON) homogenizer. The homogenate was then transferred into plastic bags and stored at 4° C. for 14 days. The meat samples were taken on day 0, 3, 5, 7, and 14 for measurement of oxidation in terms of TBARS (thiobarbituric acid reactive substances) formation.

TBARS values were determined as described by Shahidi and Hong (Shahidi, F. and Hong, C. Evaluation of malonaldehyde as a marker of oxidative rancidity in meat products. *J. Food Biochem.* 15, 97-105, 1991).

A series of TMP (1,1,3,3-tetramethoxypropane) standard solutions at difference concentrations was mixed with thiobarbituric acid (TBA) in screw-capped tubes and heated in a boiling water bath for 45 min. After cooling on ice, the absorbance was recorded at 532 nm and a standard curve was constructed (absorbance versus concentration). For TBARS in the cooked meat model system, 2 g of meat were mixed with 5 ml of trichloroacetic acid (TCA, 10% w/v) in a centrifuge tube, followed by addition of 5 ml of TBA reagent. The mixture was centrifuged at 3000×g for 10 min and the supernatant was filtered. The filtrate was heated in a boiling water bath for 45 min and absorbance was measured at 532 nm after cooling to room temperature. TBARS values in meat samples were obtained using the standard curve as μmol malonaldehyde equivalents/kg of meat. Antioxidant activity was calculated as percentage inhibition of TBARS formation by test compounds.

Discussion

As seen in Table 4, the compounds 1c>1b≥1a possess a higher percent inhibition of β-carotene than EGCG.

The compounds 1a>1b≥1c possess higher TBARS formation than EGCG. Lipophilicity of antioxidants appeared to be positively associated with their activity in cooked muscle food, as in oil-in-water emulsions.

Example 5

Antioxidant Activity of EGCG and its Fatty Acid Derivatives 1a-1c in Biological Model Systems (5a) Inhibition of LDL-Cholesterol Oxidation Human LDL solution was dialyzed overnight in PBS (10 mM, 0.15M NaCl, pH 7.4) at 4° C. under nitrogen blanket prior to the test. Sample solutions were prepared by dissolving the test compounds in ethanol at concentration of 500 μM. Ten microliters of sample solutions were transferred into a set of Eppendorf tubes, and the solvent was evaporated to dryness under a nitrogen stream. To each tube 0.1 ml of PBS was added, followed by vortexing for 1 min. An aliquot (0.8 ml) of the dialyzed and diluted LDL solution (0.125 mg/ml) was added to each tube, and the contents were mixed well and incubated at 37° C. for 15 min. The reaction was initiated by adding 0.1 ml of $CuSO_4$ (20 μM, previously incubated). A blank containing only sample without LDL or $CuSO_4$ was prepared for each test compound. After incubation of the reaction mixture at 37° C. for 22 hours, the conjugated dienes formed as a result of oxidation were measured spectrophotometrically at 234 nm. Antioxidant activities of test compounds were expressed as percentage inhibition of conjugated diene formation, which was calculated as follows.

% inhibition=100×($Abs._{control}$−$Abs._{sample}$)/ ($Abs._{control}$−$Abs._{native LDL}$)

where, control had LDL and $CuSO_4$ without antioxidants, and native LDL contained LDL only. All absorbances for samples were blank-corrected.

Discussion

As seen in Table 5, compounds 1a>1b≥(1c) possessed antioxidant activity in inhibiting LDL-cholesterol oxidation. Without being bound by theory, the inhibitory activity of the derivatives against LDL oxidation may be due to their greater lipophilicity, hence greater affinity to the phospholipids which are the major components of the surface region of LDL. Moreover, introduction of hydrophobic fatty acid side chains into the water soluble EGCG may improve its amphiphilic nature, thus allowing the derivatives to exert their antioxidant activities within the LDL particle and/or on the surface or extraparticle environment of LDL.

(5b) Inhibition of DNA Scission

For hydroxyl radical-induced DNA oxidation, 2 μL of test compounds dissolved in ethanol were added into an Eppendorf tube and the solvent was evaporated under a nitrogen stream. To the tube 2 μL of distilled water were added, followed by thorough vortexing for 1 min. The following reagents were then added to the tube in the order as stated: 2 μL of PBS (pH7.4), 2 μL of supercoiled pBR322 DNA, 2 μL of $H_2O_2$ and 2 μL of $Fe_2SO_4$. The mixture (10 μL) containing 1 μM test compounds, 0.1M PBS, 10 μg/ml DNA, 0.2 mM $H_2O_2$ and 0.1 mM $Fe_2SO_4$ (final concentration/assay) was incubated at 37° C. for 1 hour.

After incubation, 1 μL of loading dye (0.25% bromophenol blue/0.25% xylene cyanol/50% glycerol) was added, and the whole mixture was loaded onto an agarose gel. The agarose gel was prepared by dissolving 0.7% (w/v) agarose in Trisacetic acid-EDTA buffer (TAE, pH 8.5) and stained with SYBR safe gel stain. Gel electrophoresis was performed at 80V for 90 min in TAE buffer using a horizontal submarine gel electrophoresis apparatus. The bands were visualized under UV light and the images were photographed by a GelDoc apparatus equipped with a Sony digital camera. The images were analyzed using AlphaEase stand-alone software (Alpha Innotech Co., San Leandro, Calif.) and the intensity or density of the bands (obtained from densitometer) was used as the indicator of concentration of the native (supercoiled) and nicked DNA fractions. Antioxidant activity was calculated as DNA retention according to the following equation:

% retention=100×(native $DNA_{sample}$/native $DNA_{blank}$)

where, $DNA_{sample}$ and $DNA_{blank}$ are normalized concentrations of native supercoiled DNA in total DNA for sample groups and blank, respectively.

Discussion

As shown in FIG. 2, 1a-1c (referred to in the figure as 1, 2 and 3 respectively) had higher antioxidant activity against hydroxyl radical-induced DNA scission with the compound 1b being the most potent antioxidant among all.

(5c) Peroxyl Radical-Induced DNA Scission

For peroxyl radical-induced DNA oxidation, a higher concentration of samples was used, and $H_2O_2$ and $Fe_2SO_4$ were replaced with 4 μL of MPH [2,2'-azobis(2-aminopropane) dihydrochloride]. The reaction mixture contained 10 M test compounds, 0.1 M PBS, 10 μg/ml DNA and 9 mM MPH. A blank (DNA only) and a control (DNA+free radicals) were also prepared for both assays.

After incubation, 1 μL of loading dye (0.25% bromophenol blue/0.25% xylene cyanol/50% glycerol) was added, and the whole mixture was loaded onto an agarose gel. The agarose gel was prepared by dissolving 0.7% (w/v) agarose in Trisacetic acid-EDTA buffer (TAE, pH 8.5) and stained with SYBR safe gel stain. Gel electrophoresis was performed at 80V for 90 min in TAE buffer using a horizontal submarine gel electrophoresis apparatus. The bands were visualized under UV light and the images were photographed by a GelDoc apparatus equipped with a Sony digital camera. The images were analyzed using AlphaEase stand-alone software (Alpha Innotech Co., San Leandro, Calif.) and the intensity or density of the bands (obtained from densitometer) was used as the indicator of concentration of the native (supercoiled) and nicked DNA fractions. Antioxidant activity was calculated as DNA retention according to the following equation:

% retention=100×(native $DNA_{sample}$/native $DNA_{blank}$)

where, $DNA_{sample}$ and $DNA_{blank}$ are normalized concentrations of native supercoiled DNA in total DNA for sample groups and blank, respectively.

Discussion

As shown in FIG. 3, 1a-1c (referred to in the figure as 1, 2 and 3 respectively), showed protection (50.75-82.84% DNA retention) against peroxyl radical induced DNA scission.

Example 6

Incorporation of EGCG and its Fatty Acid Derivatives 1a-1c into Liposomes

Phosphotidylcholine (PC) (25 mg) was dissolved in a small amount of chloroform in a round bottom flask, followed by evaporation of the solvent with a rotary evaporator to obtain a thin layer film on the inner surface of the flask. Trace solvent was removed by nitrogen flush. An aqueous glucose solution (300 mM, 5 ml) was added to the flask, and the content was thoroughly vortexed and sonicated in an ultrosonicator, followed by a repeated freeze-thaw processing (4 times). The liposomal solution was diluted with 45 ml of phosphate buffer saline (PBS, 50 mM, pH7.4) and transferred into a centrifuge tube. The content was centrifuged at 13000 g for 5 min to remove the untrapped glucose. The sediment was re-suspended in 25 ml of PBS to obtain a final liposomal MLV. An aliquot (0.9 ml) of the above MLV was transferred to an Eppendorf tube containing 0.1 ml of test compounds (500 µM in ethanol) or ethanol blank. The content was mixed by vortexing and incubated for 20 min at 37° C. After incubation the mixture was centrifuged at 13000 g for 5 min, and the sediment was washed with 1 ml of 10% ethanol (in PBS), followed by a second centrifugation. The supernatants were combined and absorbance measured at 280 nm. A series of standard solutions in 10% ethanol at different concentrations was prepared for each test compound and their absorbance measured at 280 nm to construct a standard curve (absorbance VS. concentration). The un-incorporated test compounds in the supernatant were quantified using their corresponding standard curve. Percentage incorporation of each compound into the liposomes was calculated according to the following equation:

$$\% \text{ incorporation} = 100 \times (1 - \text{amount un-incorporated}/\text{amount added}) = 100 \times (1 - C \times 2/50)$$

where, C is the concentration of test compounds read from the standard curve.

Discussion 1a-1c had higher rates of incorporation into liposomes than EGCG, suggesting their higher cellular uptake and greater potential in liposome drug delivery systems as seen in Table 6, such that 1a>1c≥(1b)>EGCG, which is in agreement with their lipophilicity.

Example 6(a)

Inhibition Against UV-Induced Liposome Oxidation

To prepare liposome MLV, 10 mg of egg yolk PC were dissolved in a small amount of chloroform in a round bottom flask and the solvent was removed using a rotary evaporator followed by nitrogen flush. The thin film on the inner surface of the flask was suspended in 10 ml of PBS (10 mM, pH7.4, 150 mM NaCl) by vortex and sonication, and the emulsion was then repeatedly frozen and thawed for 4 times. The liposomal MLV obtained were diluted by 90 ml of PBS, and an aliquot (750 µL) was transferred into an Eppendorf tube containing 10 µL of test compounds dissolved in ethanol and 240 µL of PBS. The content was mixed well and incubated at 37° C. for 15 min. After incubation, the mixture was exposed to UV irradiation (254 nm) for 45 min. The oxidation was detected by measuring conjugated dienes (CD) spectrophotometically at 234 nm against a blank without liposome (test compounds+PBS). Conjugated diene values were calculated as follows using blank-corrected absorbances.

$$CD(\text{mol/g of } PC) = \text{Abs.}/\epsilon LC,$$

where $\epsilon$ is the absorptivity constant (29500 $M^{-1}cm^{-1}$), L is the length of the cuvette (1 cm) and C is the final concentration of PC (g/L). Antioxidant activity was then obtained as percentage inhibition of conjugation diene formation according to the following equation.

$$\% \text{ inhibition} = 100 \times (CD_{control} - CD_{sample})/CD_{control}$$

where control had only liposome and PBS without test compounds.

Discussion 1a and 1c had higher antioxidant activity against UV-induced liposome oxidation than EGCG, suggesting their potential use in skin care, as seen in Table 7.

Example 7

Anti-Inflammatory Activity of EGCG and its Fatty Acid Derivatives 1a-1c (7a) Inhibition Against iNOS and COX-2 Gene Expression in RAW 264.7 Macrophage RAW 264.7 cells were cultured in Rosewell Park Memorial Institute (RPMI) 1640 media (without phenol red) supplemented with 10% endotoxin-free, heat-inactivated fetal calf serum, 100 units/ml penicillin, and 100 µg/ml streptomycin. When the cells reached a density of $2-3 \times 10^6$ cells/ml, they were activated by incubation in a medium containing E. coli lipopolysaccharide (LPS) (100 ng/ml). Various concentrations of compounds of the disclosure in dimethyl sulphoxide (DMSO) were added together with LPS. Cells were treated with 0.05% DMSO as the vehicle control. The stimulated murine macrophage cell line RAW 264.7 cells were washed with PBS and lysed in an ice-cold RIPA buffer (Tris-HCl, pH 7.2, 25 mM; 0.1% SDS; 1% Triton X-100; 1% sodium deoxycholate; 0.15 M NaCl; 1 mM EDTA) containing 1 mM phenylmethyl sulphonyl fluoride (PMSF), 10 µg/mL aprotinin, 1 mM sodium ortho-vanadate, and 5 µg/mL leupeptin. Protein concentrations were determined using the BCA method (Pierce, Rockford, Ill.). The samples (50 µg of protein) were mixed with 5-fold of sample buffer containing 0.3 M Tris-HCl (pH 6.8), 25% 2-mercaptoethanol, 12% sodium dodecyl sulphate (SDS), 25 mM EDTA, 20% glycerol, and 0.1% bromophenol blue. The mixtures were boiled at 100° C. for 5 min, prerun on a stacking gel, and then resolved by 12% SDS-polyacrylamide minigels at a constant current of 20 mA. For western blot, proteins on the gel were electro-transferred onto a 45 µm immobile polyvinylidene fluoride (PVDF) membrane with a transfer buffer composed of 25 mM Tris-HCl (pH 8.9), 192 mM glycine, and 20% methanol, as described by Pan et al. (2000). Membrane blocking was then carried out at room temperature for 1 h in blocking solution (20 mM Tris-HCl pH 7.4, 125 mM NaCl, 0.2% Tween 20, 1% bovine serum albumin, and 0.1% sodium azide). The membrane was incubated with the primary antibody of iNOS and COX-2 at 4° C. overnight. The membranes were subsequently probed with selected IgG antibody conjugated to horseradish peroxidase (Transduction Laboratories, Lexington, Ky.) and visualized using enhanced chemiluminescence (ECL, Amersham). The densities of the bands were quantitated using a densitometer (AlphaImager 2200 System). All the membranes were stripped and reprobed for β-actin (Sigma Chemical Co., St. Louis, Mo.) as loading control.

Discussion

Figure 4:
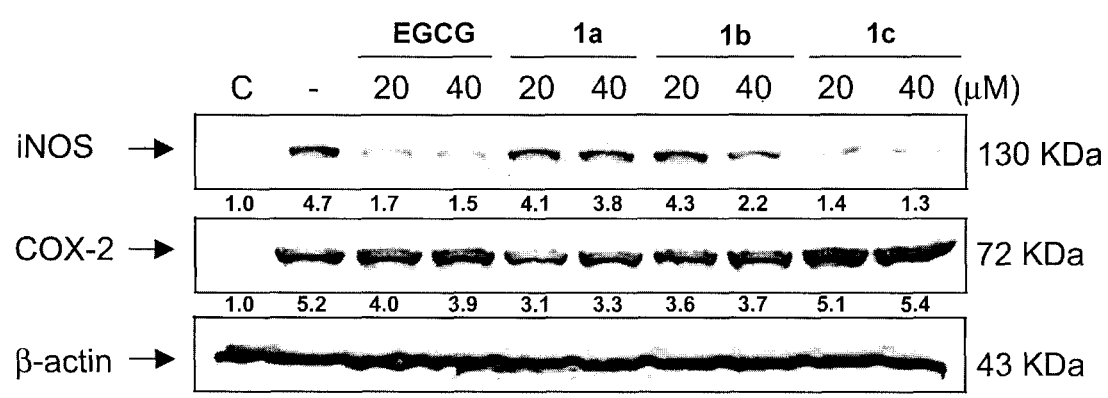
FIG. 4 shows the anti-inflammatory activity of compounds of the formula (I) in the inhibition of iNOS and COX-2 protein expression in murine macrophages.
Figure 5:
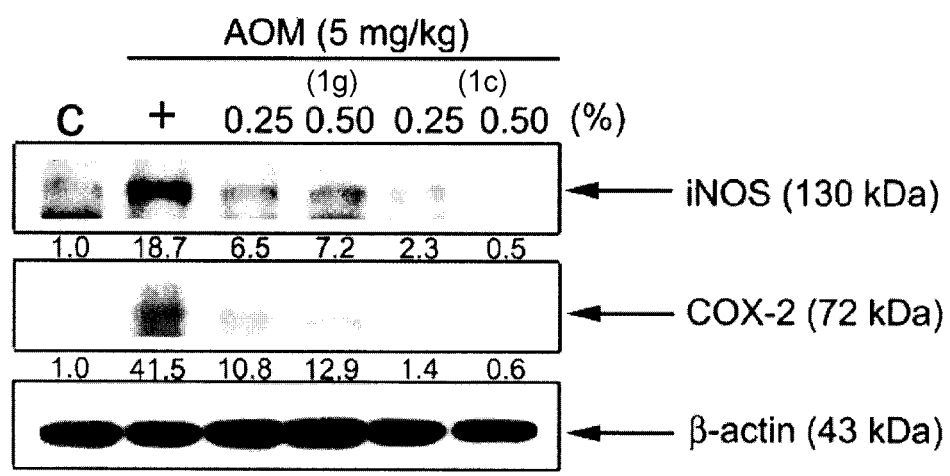
FIG. 5 shows the effect of compounds of the formula (I) on iNOS and COX-2 protein expression in azoxymethane (AOM)-treated mice.

According to the results from western blotting (as seen in FIG. 4), LPS increased the protein level of both cytokines, and the compounds of the disclosure were able to attenuate the increase caused by LPS, depending on the concentration. For iNOS, 1b showed a strong dose-dependent relationship in suppressing the cytokine production between the two concentrations tested (20 and 40 µM), i.e. higher concentration of the compound resulted in lower level of iNOS; while the suppressing effect was not distinctively different at the two concentrations for other compounds (see FIG. 5). 1c was the most potent in inhibiting the induction of iNOS expression. The inhibition of iNOS induction by compounds of the disclosure may be due to down regulation of iNOS gene expression. EGCG and compounds of the disclosure with antioxidant activities may inhibit the ROS/RNS-mediated activation of NF-κB, the transcription factor that promotes gene expression of iNOS.

Figure 3:
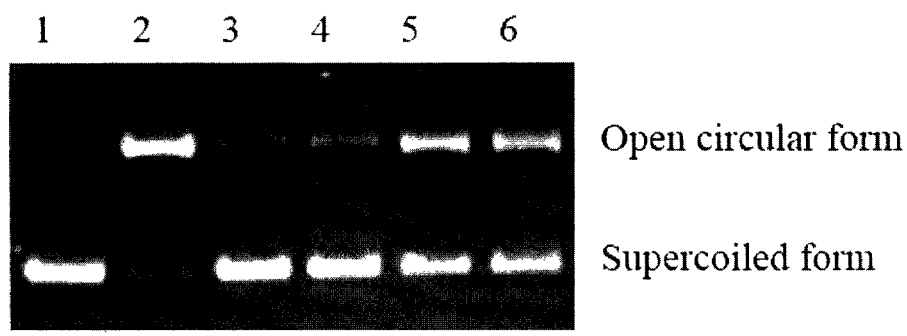
FIG. 3 shows the antioxidant activity of compounds of the formula (I) in peroxyl radical-induced DNA scission.

The macrophages treated with EGCG and compounds of the disclosure showed altered levels of COX-2 compared to those treated with LPS alone (see FIG. 3). Their inhibitory effect decreased in the order of 1a>1b>EGCG>1c, which is opposite to that observed for iNOS inhibition. The difference in their ability to inhibit production of iNOS and COX-2 may be due to other mechanisms involved in addition to blocking the NF-κB signalling pathway. EGCG and its derivatives may also suppress the cytokine production by breaking down the mRNA and protein of iNOS and COX-2 to varied degrees.

(7b) Inhibition Against LPS-Induced NO Production in RAW 264.7 Macrophage

The LPS-induced NO production by the macrophages was determined as nitrite concentration in the culture medium according to the Griess reaction. The culture medium of the control and treated cells was collected and centrifuged. An aliquot (100 μL) of the supernatant was mixed with an equal volume of Griess reagent. The absorbance of the mixture at 550 nm was measured with an ELISA plate reader (Dynatech MR-7000; Dynatech Laboratories, Chantilly, Va., USA).

Discussion

Excessive and uncontrolled production of NO in activated immune cells during inflammation contributes to the major destructive force in tissue injury. NO production by immune cells has been used as an indicator for the presence and extent of inflammation as well as the effectiveness of anti-inflammatory agents. Compounds 1a-1c were able to inhibit NO production in the stimulated macrophages in a dose-dependent manner, as seen in Table 8. EGCG had the highest $IC_{50}$ (103.3 μM) among all. Compounds 1c>1b>1a, showed greater efficiency than the parent EGCG molecule in inhibiting NO production, with low $IC_{50}$ ranging from 29.8 to 40.7 μM. Among the compounds, the esters with polyunsaturated side chains ((1b) and (1c)) had slightly lower $IC_{50}$ than the stearate (1a) with saturated side chain. Without being bound by theory, the steric characteristics of the derivatives, especially those of compounds 1b and 1c with bending fatty acid side chains, may favor iNOS binding and account for greater inhibition of the enzyme activity than that exerted by EGCG.

Example 8

Antiviral Activity of EGCG and its Derivatives (8a): Inhibition Against HCV Protease An aliquot (2 μl) of test compounds dissolved in DMSO was added to each well of a 384-well black Assay plate, followed by addition of 8 μl of HCV NS3/4A protease solution (0.5 μg/ml). The reaction was initiated by adding 10 μl of freshly diluted substrate (100× dilution of a DMSO stocking solution). The mixture was incubated at room temperature for 30 min, and the fluorescence intensity was measured at 485 nm for excitation and 535 nm for emission by a TECAN GENios plate reader. Inhibitory activity of test compounds was calculated as inhibition percentage according to the following equation:

$$\% \text{ inhibition}=100\times(F_{control}-F_{sample})/F_{control}$$

where, $F_{control}$ and $F_{sample}$ stand for the fluorescence value of control without test compounds and of those with added test compounds. All fluorescence values were corrected with a substrate blank. Samples were assayed at different concentrations to plot a concentration VS. inhibition percentage curve, and $IC_{50}$ values were obtained from the curve for each sample. A known HCV protease inhibitor, embelin, was used as a reference.

Discussion

EGCG did not show any significant effect in inhibiting the protease, having a high $IC_{50}$ value of >200 μM compared to that of the positive control embelin (10.19 μM), as shown in Table 9. However, inhibition was observed for compounds 1b and 1c containing omega-3 PUFA which displayed a protease inhibitory activity that was 1700-fold stronger than that of embelin. Although less effective than compounds 1b and 1c, compound 1a inhibited the protease to approximately 80-fold higher than embelin. The compound 1(g) with all 8 hydroxyl groups occupied with short chain acyl moieties was not expected to possess any antioxidant activity due to absence of the functional OH groups. However, it exhibited a protease inhibitory activity 10-fold stronger than that of embelin. Without being bound by theory, the ability of EGCG derivatives in inhibiting HCV protease may arise from the changes in steric features and hydrophilic-lipophilic balance (HLB) of the molecules leading to the superior binding affinity to the enzyme.

(8b): Inhibition Against α-glucosidase

To each well of a 96-well plate 40 μl of 4-nitrophenyl α-D-glucopyranoside (2 mM, dissolved in 100 mM potassium phosphate buffer, pH 7.0) and 5 μl of sample solution (in DMSO) were added. The reaction was initiated by adding 5 μl of the enzyme solution (0.3 μu/ml α-glucosidase from *Bacillus stearothermophilus*). The plate was incubated at 37° C. for 20 min, and the absorbance was measured before and after incubation at 405 nm with an InterMed ImmunoReader (Nippon InterMed K.K. Tokyo, Japan). The absorbance change (ΔA) was recorded and compared between control and samples. The inhibitory activity of test compounds against α-glucosidase was calculated as follow:

$$\% \text{ inhibition}=100\times(\Delta A_{control}-\Delta A_{sample})/\Delta A_{control}$$

where, $\Delta A_{control}$ and $\Delta A_{sample}$ represent the absorbance change after incubation of the control (DMSO only) and samples, respectively. Acarbose was used as a reference inhibitor for α-glucosidase.

Discussion

As shown in Table 10, 1a-1c and 1(g) had greater α-glucosidase inhibitory activity than EGCG, and therefore are useful for the inhibition of α-glucosidase, which is present in HIV. Compound 1a had the lowest IC50 value i.e. highest potency as α-glucosidase inhibitor among all derivatives, followed by compound 1(g). The results suggest that the binding affinity of EGCG and its derivatives to α-glucosidase may be dependent on a combined factor of hydrophobic interaction and steric features, Example 9

Anti-Cancer Activity of EGCG Derivatives

9(a): Animal Studies

Figure 6:
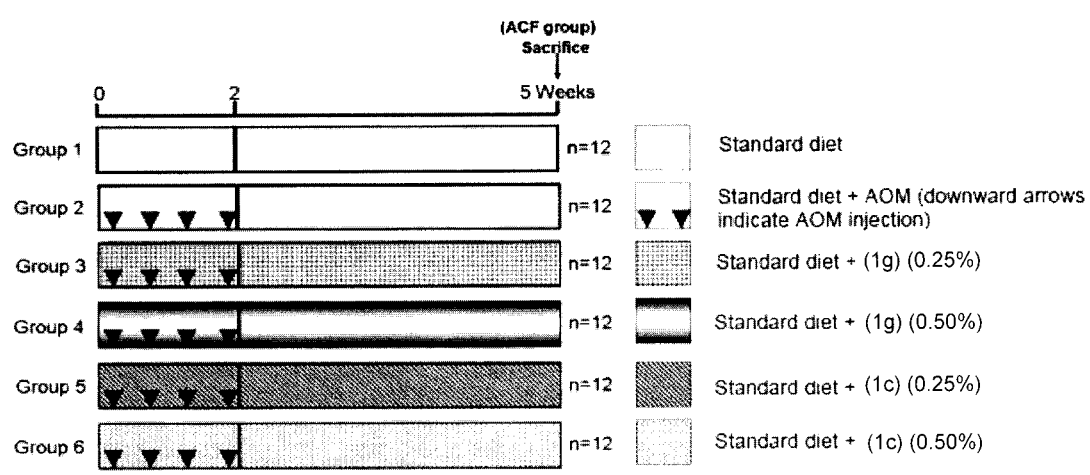
FIG. 6 is a diagram showing the experimental design to determine the anti-cancer activity of compounds of the formula (I)

Male ICR mice at 5 weeks of age were purchased from the BioLASCO Experimental Animal Center (Taiwan Co., Ltd). After 1 week of acclimation, animals were randomly distributed into control and experimental groups. All animals were housed in a controlled atmosphere (25±1° C. at 50% relative humidity) and with a 12-hour light/12-hour dark cycle. Animals had free access to food and water at all times. Food cups were replenished with fresh diet every day. The experimental protocol is illustrated in FIG. 6. Mice were divided into 6 groups. One group (negative control) was fed standard diet; one group (positive control) was fed standard diet but injected with azozymethane (AOM) twice a week for 2 weeks; the remaining 4 groups had AOM injection and dietary supplementation of different levels of EGCG esters (1a and EGCG-DHA ester mixture containing predominantly 1c and its homologues).

9(b): Identification of ACF

The formalin-fixed colonic tissues were cut into proximal (1-2 cm from the cecum), middle (3-4 cm) and distal (1-2 cm from anus) segments and stained in 0.2% methylene blue solution for 10 min. Methylene blue-stained ACF in each focus were counted under a microscope (×40). The ACF location (distance from anus) and size (number of aberrant crypts) were recorded.

9(c): Western Blot Analysis

For protein analyses, total scraped colon mucosa was homogenized on ice for 15 s with a Polytron tissue homogenizer and lysed in 0.5 mL ice-cold lysis buffer [50 mM Tris-HCl, pH 7.4, 1 mM NaF, 150 mM NaCl, 1 mM EGTA, 1 mM phenylmethane-sulphonyl fluoride, 1% NP-40, and 10 mg/mL leupeptin] on ice for 30 min, followed by centrifugation at 10,000 g for 30 min at 4° C. The samples (50 mg of protein) were mixed with 5× sample buffer containing 0.3 M Tris-HCl (pH 6.8), 25% 2-mercapto-ethanol, 12% sodium dodecyl sulphate (SDS), 25 mM EDTA, 20% glycerol, and 0.1% bromophenol blue. The mixtures were boiled at 100° C. for 5 min and were subjected to stacking gel then resolved by 12% SDS-polyacrylamide minigels at a constant current of 20 mA. Subsequently, electrophoresis was carried out on SDS-polyacrylamide gels. For Western Blot analysis, proteins on the gel were electrotransferred onto the 45 micron immobile membrane (PVDF; Millipore Corp., Bedford, Mass.) with transfer buffer composed of 25 mM Tris-HCl (pH 8.9), 192 mM glycine, and 20% methanol. The membranes were blocked with blocking solution (20 mM Tris-HCl pH 7.4, 0.2% Tween 20, 1% bovine serum albumin, and 0.1% sodium azide). The membrane was further incubated with respective specific antibodies, at appropriate dilution (1:1000) using blocking solution with the primary antibody of iNOS, COX-2 monoclonal antibodies (Transduction Laboratories, BD) overnight at 4° C. The membranes were subsequently probed with anti-mouse or anti-rabbit IgG antibody conjugated to horseradish peroxidase (Transduction Laboratories, Lexington, Ky.) and visualized using enhanced chemiluminescence (ECU, Amersham). The densities of the bands were quantitated with a computer densitometer (AlphaImager™ 2200 System). All the membranes were stripped and reprobed for β-actin (Sigma Chemical Co.) as loading control.

Discussion

Figure 7:
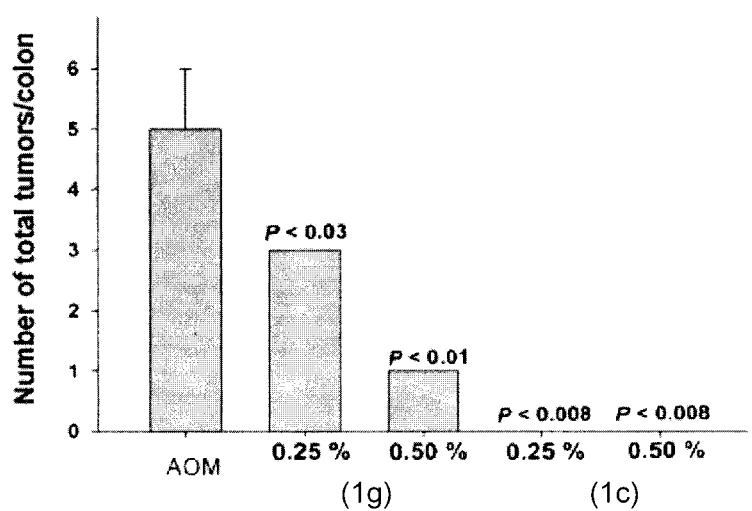
FIG. 7 is a graph showing the effect of compounds of the formula (I) on colon tumors in AOM treated mice.
Figure 8:
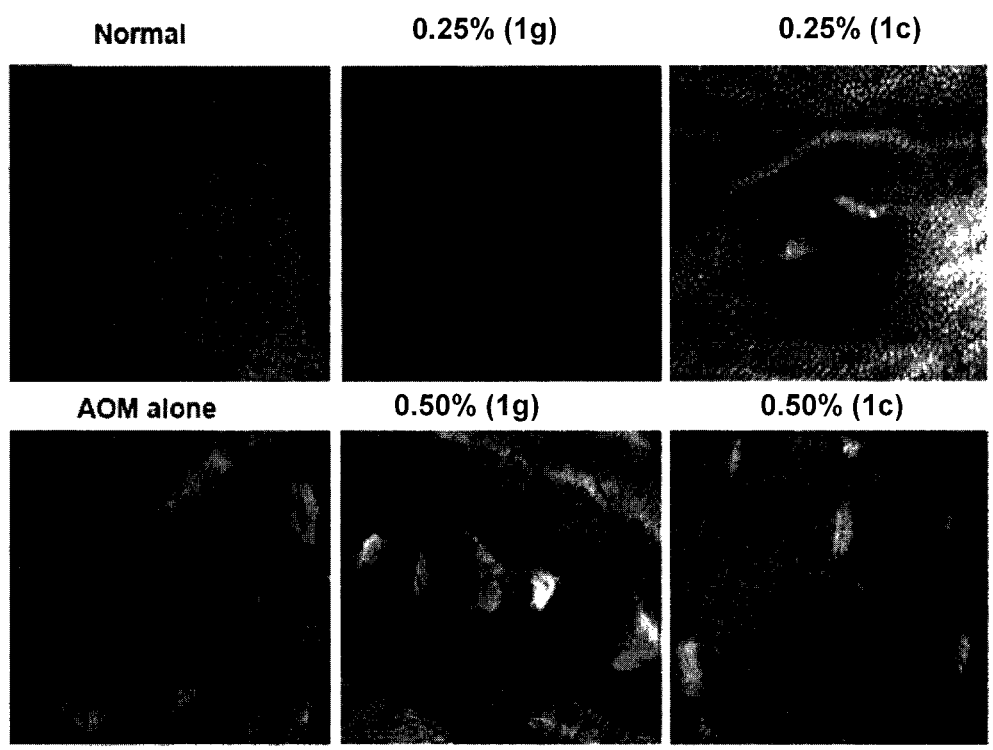
FIG. 8 shows the morphology of normal and aberrant crypts on colon of mice given compounds of formula (I) in an embodiment of the disclosure.

Colorectal cancer (CRC) is the second most often diagnosed cancer and a significant cause of mortality in western countries. Colonic aberrant crypt foci (ACF) are identified as intermediate precancerous lesions and precursors of adenoma and cancer, and may serve as predictive biomarkers of CRC. In the rat model, the ACF was enhanced by cancer promoters such as azoxymethane (AOM) and suppressed by chemopreventive agents. It has been widely accepted that the incidence of ACF in rodents correlates strongly with the final tumour outcome. In humans, significant correlation has also been established between the number of ACF, the size of the foci, the presence of dysplastic foci and the number of adenomas. Compound 1(g) and EGCG-DHA crude ester mixture (contain predominantly 1c and its homologues) significantly suppressed tumorogenesis in mice in terms of number and size of ACF. Further, as seen in FIG. 7, the colon tumors were arrested by DHA ester of EGCG and inhibited to a lesser level by 1(g). FIG. 8 shows the morphology of colon ACF as affected by 1(g) and EGCG-DHA. iNOS and COX-2 as indicators of carcinogenesis were also inhibited at the expressional level. As seen in FIG. 7, 1(g) and EGCG-DHA show a dose-dependent inhibitory effect against iNOS and COX-2 expression in mice colon.

Example 10

Preparation of EGCG Ester with Docosapentaenoic Acid

Docosapentaenoic acid (DPA) was used for acylation to EGCG-docosapentaenoate. DPA was converted to its corresponding acyl chloride by reacting with thionyl chloride. Esterification of EGCG was carried out with the acyl chlorides at a mole ratio of 1:1. Acyl chloride was added dropwise to EGCG dissolved in ethyl acetate, and the reaction was catalyzed by pyridine, which removed the released HCl from the medium. The mixture was then heated in an oil bath at 50° C. and under a nitrogen blanket with constant stirring. The reaction mixture upon completion of the esterification was cooled to ambient temperature and filtered. The filtrate was then washed 3 times with distilled water (60° C.), and the ethyl acetate layer was collected and passed through a cone of anhydrous sodium sulphate. The dry powder of crude products containing a mixture of EGCG esters (at different degrees of substitution) was obtained by removing the solvent, using a rotary evaporator, to provide 10a.

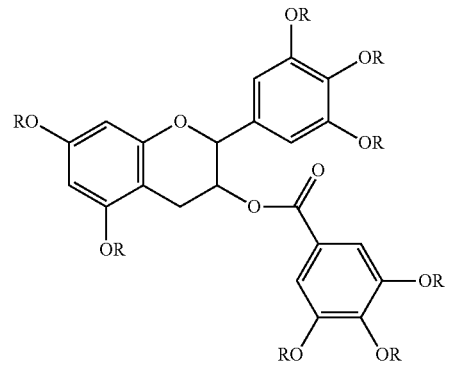

(10a)

R = CO(CH$_2$)$_5$(CH=CHCH$_2$)$_5$CH$_3$ at some positions, and H at others.

Example 11

Figure 9:
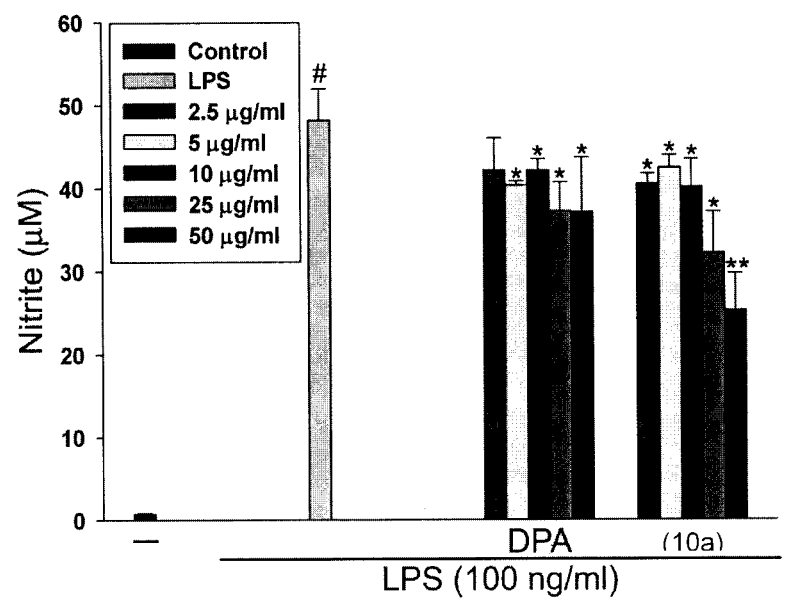
FIG. 9 demonstrates the effect of a compound of the formula (I) on NO production in LPS-stimulated RAW264.7 macrophages.

Effect of DPA and 10a on Inflammatory Mediators (11a) Effect of DPA and 10a (EGCG-DPA) on NO Production Analysis of 10a on the effect on NO production in LPS-stimulated RAW264.7 macrophages was carried out using the procedure of Example 7b. FIG. 9 illustrates that the production of the inflammatory mediator NO was inhibited by 10a (EGCG-DPA) more effectively than DPA, through the inhibition of iNOS. Without being bound by theory, in addition, the EGCG moiety in the ester may render a direct scavenging effect on NO, and the lipophilic DPA moiety may contribute to a higher affinity of the molecule to the lipid soluble free radical.

(11b) Effect of DPA and 10a (EGCG-DPA) on PGE$_2$ Production

Figure 10:
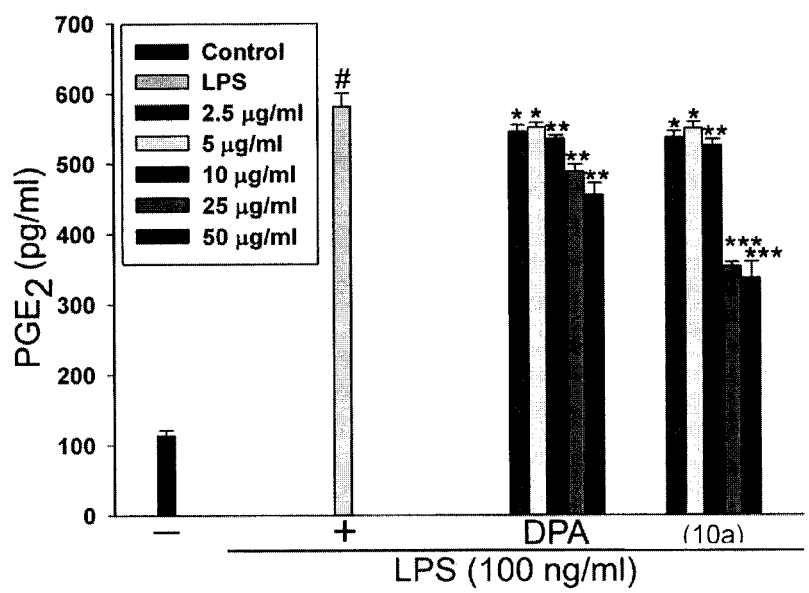
FIG. 10 demonstrates the effect of a compound of the formula (I) on prostaglandin $E_2$ ($PGE_2$) production in LPS-stimulated RAW264.7 macrophages.

The level of PGE$_2$ released into the culture medium was quantified by a specific enzyme immunoassay (EIA) method using a ACE™ EIA kit according to the manufacturer's instructions. FIG. 10 illustrates that the production of the inflammatory mediator $PGE_2$ was inhibited by 10a (EGCG-DPA). The EGCG ester 10a has improved lipophilicity and cellular absorption, and therefore provides synergistic effects with respect to the DPA (a competitive inhibitor against the omega-6 fatty acid arachidonic acid) for the COX enzymes) and EGCG (COX-2 inhibitor) moieties.

Example 12

Effect of DPA and 10a (EGCG-DPA) on Expression of iNOS and COX-2 Proteins

Figure 11:
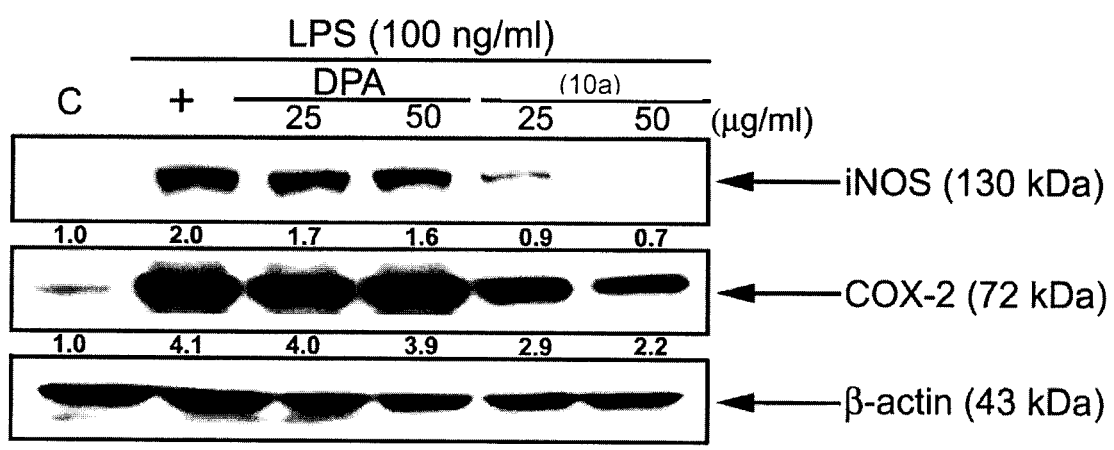
FIG. 11 demonstrates the effect of a compound of the formula (I) on expression of iNOS and COX-2 proteins in LPS-stimulated RAW264.7 macrophages.

Analysis of 10a on the effect on expression of iNOS and COX-2 proteins in LPS-stimulated RAW264.7 macrophages was carried out using the procedure of Example 7a. FIG. 11 illustrates that the expression of iNOS and COX-2 proteins is inhibited by 10a (EGCG-DPA). Without being bound by theory, the inhibition of iNOS and COX-2 induction by 10a is thought to be due to the down-regulation of their gene expression at transcriptional level. Gene expression of iNOS and COX-2 is promoted by the transcription factor NF-κB and AP-1, which are redox-sensitive and become activated under oxidative stress. The EGCG-DPA esters with antioxidant potential (as reported for compounds 1a-1c) is thought to alleviate oxidative stress and inhibit activation and/or translocation of NF-κB and AP-1, thus down-regulating the expression of the iNOS and COX-2 genes.

Example 13

Effect of DPA and 10a (EGCG-DPA) on Expression of iNOS and COX-2 mRNA by Reverse Transcriptase Polymerase Chain Reaction (RT-PCR)

Total RNA was isolated from mouse macrophage RAW264.7 cell using Trizol Reagent according to the manufacturer's instructions. Changes in the steady-state concentration of mRNA in iNOS, COX-2, and β-actin (control) were assessed by RT-PCR. Total RNA (2 µg) was converted to cDNA in a series of standard 10 µl reverse transcription reactions. DNA amplification was carried out in "Ready To Go" PCR Beads. The initial conditions were 95° C. for 5 min. Amplification 30 cycles of iNOS were 95° C. for 40 s, 65° C. for 60 s, and 72° C. for 2 min, followed by a 10 min extension at 72° C. The thermal cycle conditions of COX-2 were initiated at 95° C. for 60 min, then 30 cycles of amplification (94° C. for 45 s, 55° C. for 60 s, and 72° C. for 2 min) were performed followed by 10 min extension at 72° C. The PCR products were separated by electrophoresis on a 1% agarose gel and visualized by ethidium bromide staining. Amplification of β-actin served as a control for sample loading and integrity. PCR was performed on the cDNA using the following sense and antisense primer: iNOS, forward primer 5'-CCCTTCCGAAGTTTC-TGGCAGCAGC-3' (2944-2968), reverse primer 5'-GGCTGTCAGAGCCTCG-TG-GCTTTGG-3' (3419-3443); COX-2, forward primer 5'-GGAGAGACTATCAAGA-TAGTGATC-3' (1094-1117), reverse primer 5'-ATGGTCAGTAGACTTTTACAGCTC-3' (1931-1954); β-actin, forward primer 5'-AAGAGAG-GCATCCTCACCCT-3', reverse primer 5'-TACATG-GCTGGGGTGTTGAA-3'. Confirmation of the correct amplicons was obtained by direct DNA sequencing of the PCR products.

Discussion

Figure 12:
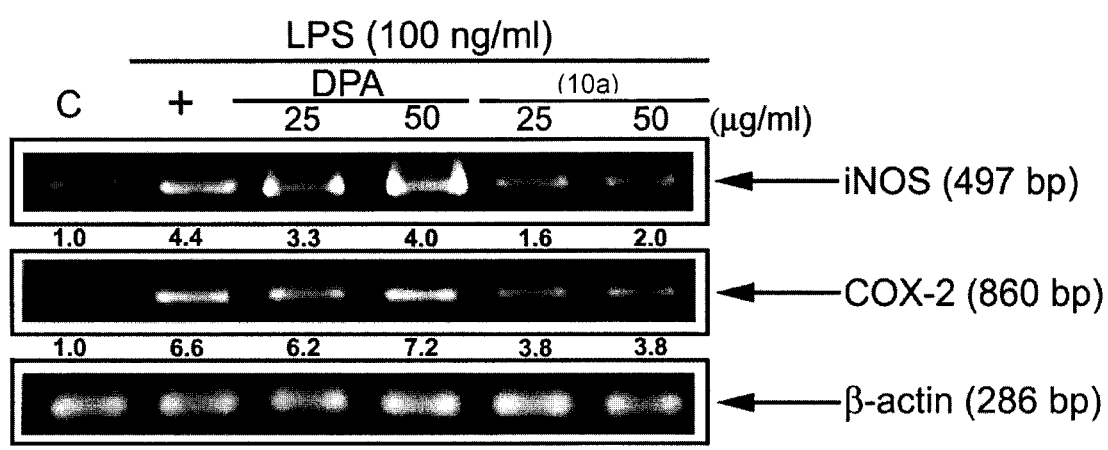
FIG. 12 demonstrates the effect of a compound of the formula (I) on expression of iNOS and COX-2 mRNA in LPS-stimulated RAW264.7 macrophages.

FIG. 12 illustrates that the expression of iNOS and COX-2 mRNA is inhibited by 10a (EGCG-DPA). Without being bound by theory, the down-regulation effect of 10a on the two inflammatory mediators is thought to arise from their EGCG moiety, which has been demonstrated to inhibit the activation of transcription factors NF-κB and AP-1 through various mechanisms.

TABLE 1

Lipophilicity (partition coefficient, P) of EGCG and fatty acid derivatives 1a-1c

| Compounds | EGCG | 1a | 1b | 1c |
|---|---|---|---|---|
| P | $0.48 \pm 0.01^{c}$ | $1.42 \pm 0.02^{a}$ | $1.10 \pm 0.06^{b}$ | $1.03 \pm 0.10^{b}$ |

TABLE 2

Antioxidant activity of EGCG and fatty derivatives 1a-1c by in vitro chemical assays

| Assay | EGCG | 1a | 1b | 1c |
|---|---|---|---|---|
| DPPH scavenging (mmol trolox eq./mol) | 3.13 | 5.85 | 4.66 | 5.09 |
| ORAC (mol trolox eq./mol) | 14.97 | 51.56 | 81.52 | 84.70 |
| Metal chelation (%) | 10.42 | 8.33 | 35.42 | 28.13 |

TABLE 3

Antioxidant activity of EGCG and fatty acid derivatives 1a in Bulk Oil System

| | Control | EGCG | 1a | 1b | 1c |
|---|---|---|---|---|---|
| Induction Time (h) | 2.84 | 3.97 | 6.75 | 2.33 | 2.19 |
| Protection Factor (PF) | 1.00 | 1.40 | 2.38 | 0.82 | 0.77 |

TABLE 4

Oil/Water emulsion (β-carotene/linoleate) and Meat (Pork) Model System

| Inhibition (%) | EGCG | 1a | 1b | 1c | BHA |
|---|---|---|---|---|---|
| β-carotene bleaching | $7.90 \pm 0.64^{c}$ | $16.8 \pm 4.19^{b}$ | $28.0 \pm 0.17^{a}$ | $32.1 \pm 4.48^{a}$ | — |
| TBARS formation in cooked pork | $71.9 \pm 1.56^{d}$ | $86.3 \pm 2.10^{a}$ | $80.5 \pm 0.80^{bc}$ | $78.4 \pm 1.62^{c}$ | $83.3 \pm 2.34^{ab}$ |

TABLE 5

Antioxidant activity of EGCG and its fatty acid derivatives 1a-1c in inhibiting LDL-cholesterol oxidation

| | EGCG | 1a | 1b | 1c |
|---|---|---|---|---|
| Inhibition (%) | 6.53 | 16.33 | 11.80 | 8.18 |

TABLE 6

Incorporation of EGCG and its fatty acid derivatives 1a-1c into liposomes

|  | EGCG | 1a | 1b | 1c |
|---|---|---|---|---|
| % incorporation | 65.17 | 91.19 | 71.81 | 80.91 |

TABLE 7

Inhibition against UV-induced liposome oxidation

|  | EGCG | 1a | 1b | 1c |
|---|---|---|---|---|
| % inhibition | 9.53 | 47.59 | 3.47 | 16.22 |

TABLE 8

Inhibition against LPS-induced NO production in RAW 264.7 macrophage

|  | EGCG | 1a | 1b | 1c |
|---|---|---|---|---|
| $IC_{50}$ (μM) | 103.29 | 40.66 | 33.73 | 29.78 |

TABLE 9

Inhibition against HCV protease

| Compounds | EGCG | 1a | 1b | 1c | 1g | Embelin |
|---|---|---|---|---|---|---|
| $IC_{50}$ (μM) | >200 | 0.13 | 0.006 | 0.006 | 0.98 | 10.19 |
| RSD % | 5.5 | 1.8 | 3.4 | 3.0 | 4.4 | 9.0 |

RSD: Relative standard deviation

TABLE 10

Inhibition against α-glucosidase

| Compounds | EGCG | 1a | 1b | 1c | 1g | Acarbose |
|---|---|---|---|---|---|---|
| $IC_{50}$ (μM) | >200 | 2.62 | 15.66 | 15.87 | 6.87 | 0.15 |
| RSD % | | 8.0 | 1.9 | 7.0 | 2.7 | 4.7 | 5.3 |

RSD: Relative standard deviation

We claim:

1. A compound of the formula (I):

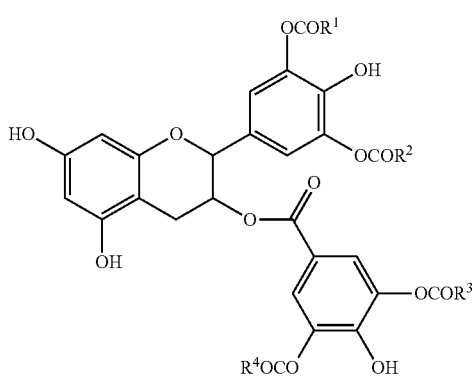

wherein
$R^1$, $R^2$, $R^3$ and $R^4$ are independently or simultaneously $C_{1-3}$alkyl, $C_{2-3}$alkenyl or an unsaturated or saturated aliphatic moiety of a 6-carbon to 22-carbon fatty acid, or a pharmaceutically acceptable salt, carbamate, solvate or stereoisomer thereof.

2. The compound of the formula (I) according to claim 1, wherein the unsaturated or saturated aliphatic moiety of the fatty acid contains between 13 and 21 carbon atoms.

3. The compound of the formula (I) according to claim 1, wherein the aliphatic moiety of the 14-carbon to 22-carbon fatty acid is unsaturated.

4. The compound of the formula (I) according to claim 1, wherein the aliphatic moiety of the 14 carbon to 22-carbon fatty acid is derived from an omega-3, omega-6 or omega-9 fatty acid.

5. The compound of the formula (I) according to claim 3, wherein the unsaturated aliphatic moiety of the 14-carbon to 22-carbon fatty acid is derived from an omega-3 fatty acid.

6. The compound of the formula (I) according to claim 5, wherein the omega-3 fatty acid is selected from 7,10,13-hexadecatrienoic acid, 9,12,15-octadecatrienoic acid, 6,9,12,15-octadecatetraenoic acid, 11,14,17-eicosatrienoic acid, 8,11,14,17-eicosatetraenoic acid, 5,8,11,14,17-eicosapentaenoic acid, 7,10,13,16,19-docosapentaenoic acid, 4,7,10,13,16,19-docosahexaenoic acid, 9,12,15,18,21-tetracosapentaaenoic acid and 6,9,12,15,18,21-tetracosahexaenoic acid.

7. The compound of the formula (I) according to claim 4, wherein the omega-6 fatty acid selected from 9,12-octadecadienoic acid, 6,9,12-octadecatrienoic acid, 11,14-eicosadienoic acid, 8,11,14-eicosatrienoic acid, 5,8,11,14-eicosatetraenoic acid, 13,16-docosadienoic acid, 7,10,13,16-docosatetraenoic acid, 4,7,10,13,16-docosapentaenoic acid and 8E,10E,12Z-octadecatrienoic acid.

8. The compound of the formula (I) according to claim 4, wherein the omega-9 fatty acid selected from 9-octadecaenoic acid, 11-eicosaenoic acid, 5,8,11-eicosatrienoic acid, 13-docosaenoic acid and 15-tetracosaenoic acid.

9. The compound of the formula (I) according to claim 1, wherein the unsaturated or saturated aliphatic moiety of the 14 carbon to 22-carbon fatty acid is selected from the formula (i), (ii), (iii) and (iv)

$$—(CH_2)_{16}CH_3 \qquad (i)$$

$$—(CH_2)_3(CH=CHCH_2)_5CH_3 \qquad (ii)$$

$$—(CH_2)_2(CH=CHCH_2)_6CH_3 \qquad (iii)$$

$$—(CH_2)_5(CH=CHCH_2)_5CH_3 \qquad (iv).$$

10. The compound of the formula (I) according to claim 1, wherein $R^1$, $R^2$, $R^3$ and $R^4$ are identical and are selected from the group consisting of $C_{1-3}$alkyl, $C_{2-3}$alkenyl and an unsaturated or saturated aliphatic moiety of a 6-carbon to 22-carbon fatty acid.

11. The compound of the formula (I) according to claim 1, wherein $R^1$, $R^2$, $R^3$ and $R^4$ are simultaneously or independently an unsaturated or saturated aliphatic moiety of a 6-carbon to 13-carbon fatty acid.

12. The compound of the formula (I) according to claim 11, wherein the aliphatic moiety of the 6-carbon to 13-carbon fatty acid is derived from a caprylic acid, caproic acid or lauric acid.

13. The compound according to claim 1, wherein the compound of the formula (I) is

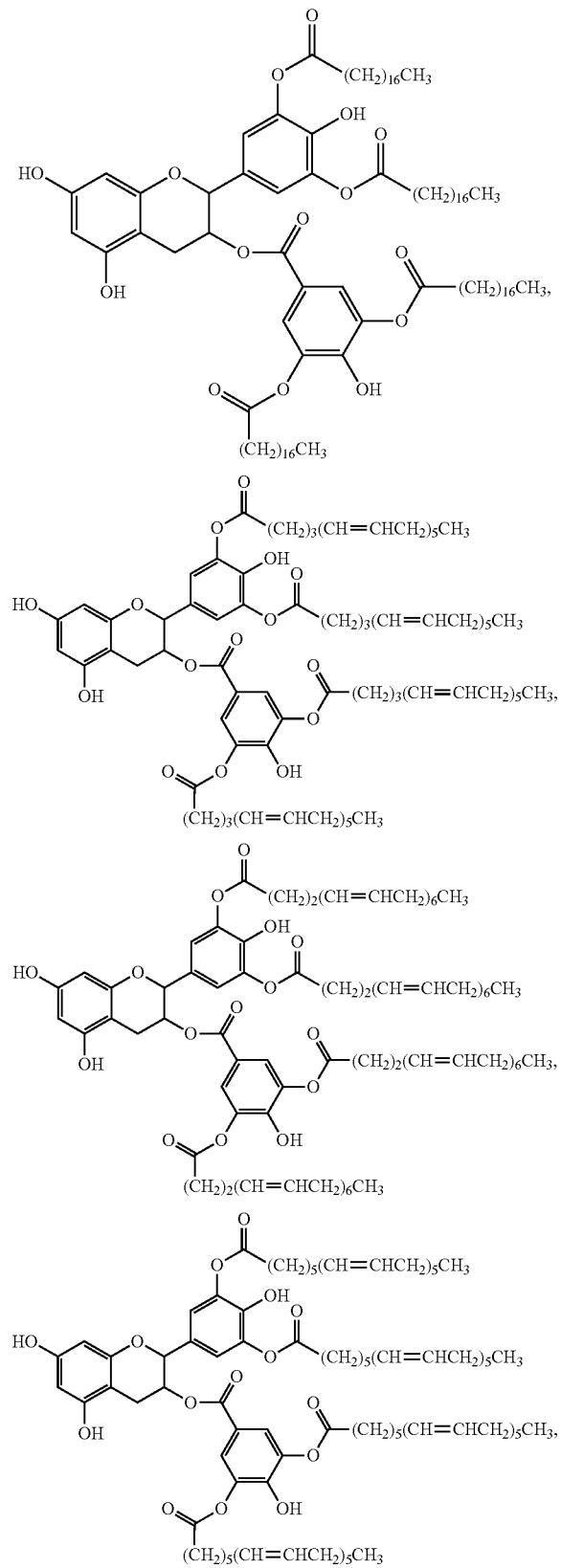

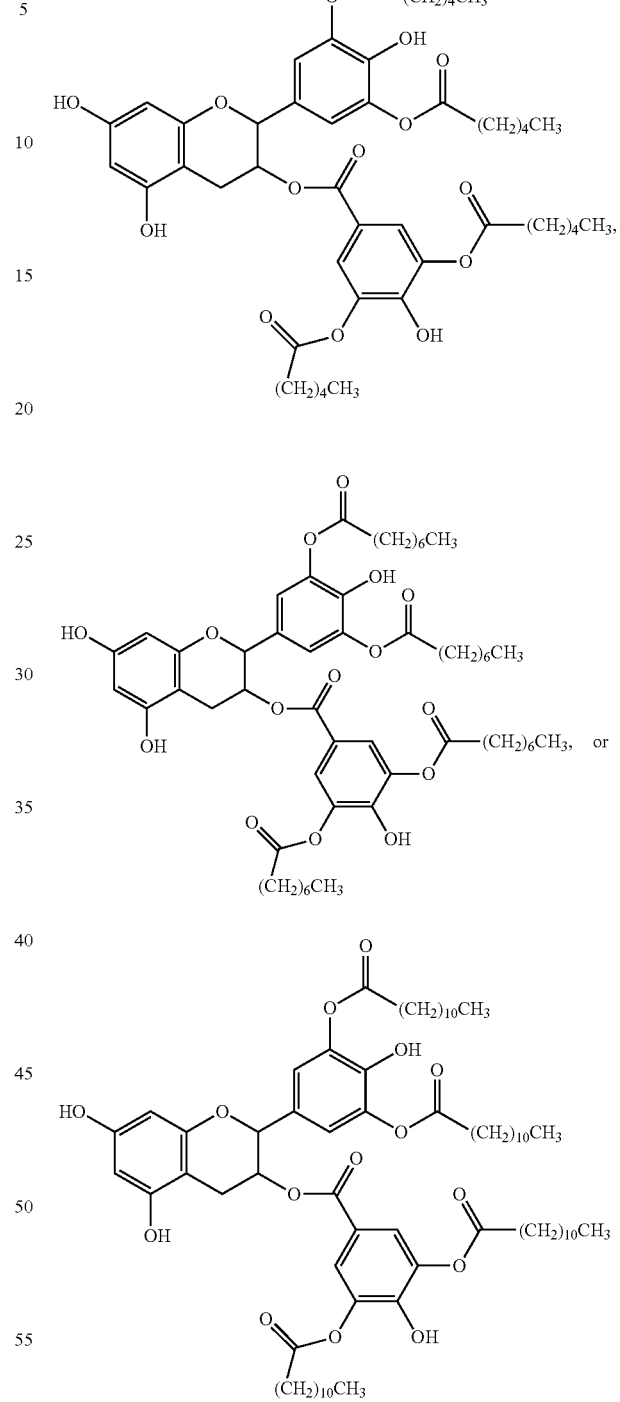

or stereoisomers thereof.

14. A method for the treatment of atherosclerosis, lipopolysaccharide-induced inflammation, hepatitis C infection, HIV infection or colon cancer in a mammal comprising administering to the mammal a therapeutically effective amount of one or more compounds of the formula (I) as claimed in claim 1.

15. A pharmaceutical composition comprising one or more compounds of the formula (I) or pharmaceutically acceptable salts, carbamates, solvates or stereoisomers thereof as claimed in claim 1, and a pharmaceutically acceptable excipient.

16. A pharmaceutical composition comprising:

(i) a compound of the formula (I)

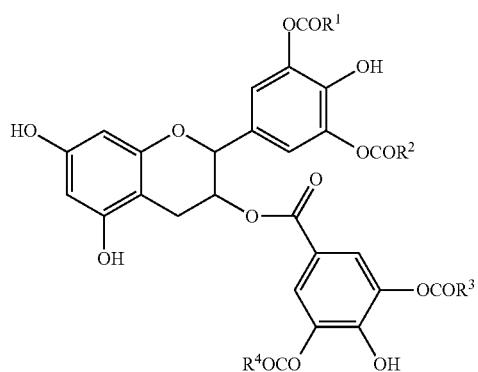

wherein $R^1$, $R^2$, $R^3$ and $R^4$ are independently or simultaneously $C_{1-3}$alkyl, $C_{2-3}$alkenyl or an unsaturated or saturated aliphatic moiety of a 6-carbon to 22-carbon fatty acid, or a pharmaceutically acceptable salt, carbamate, solvate or stereoisomer thereof; and (ii) a penta-ester and/or hexa-ester of a compound of Formula (II)

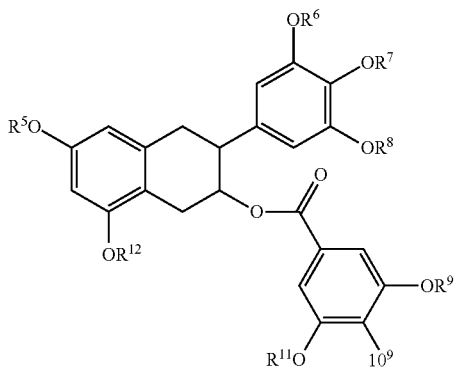

wherein $R^5$-$R^{12}$ are independently or simultaneously H or $-C(=O)R^{13}$, $R^{13}$ is independently or simultaneously $C_{1-3}$alkyl, $C_{2-3}$alkenyl or an unsaturated or saturated aliphatic moiety of a 5-carbon to 22-carbon fatty acid, or a pharmaceutically acceptable salt, carbamate, solvate or stereoisomer thereof.

17. The compound according to claim 1, wherein $R^1$, $R^2$, $R^3$ and $R^4$ are independently or simultaneously an unsaturated aliphatic moiety of a 14-carbon to 22-carbon fatty acid having four to six double bonds derived from marine or algal oils.

18. The compound according to claim 17, wherein $R^1$, $R^2$, $R^3$ and $R^4$ are independently or simultaneously derived from 6,9,12,15-octadecatetraenoic acid, 8,11,14,17-eicosatetraenoic acid, 5,8,11,14,17-eicosapentaenoic acid, 7,10,13,16,19-docosapentaenoic acid, 4,7,10,13,16,19-docosahexaenoic acid, 9,12,15,18,21-tetracosapentaaenoic acid, 6,9,12,15,18,21-tetracosahexaenoic acid, 5,8,11,14-eicosatetraenoic acid, 7,10,13,16-docosatetraenoic acid or 4,7,10,13,16-docosapentaenoic acid.

* * * * *